(12) United States Patent
Dellinger et al.

(10) Patent No.: US 6,222,030 B1
(45) Date of Patent: Apr. 24, 2001

(54) SOLID PHASE SYNTHESIS OF OLIGONUCLEOTIDES USING CARBONATE PROTECTING GROUPS AND ALPHA-EFFECT NUCLEOPHILE DEPROTECTION

(75) Inventors: Douglas J. Dellinger, Sunnyvale, CA (US); Marvin H. Caruthers, Boulder, CO (US); Jason R. Betley, Bury St. Edmunds (GB)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/338,179

(22) Filed: Jun. 22, 1999

Related U.S. Application Data

(63) Continuation-in-part of application No. 09/128,052, filed on Aug. 3, 1998.

(51) Int. Cl.[7] .......................... C07H 21/00; C07H 21/02; C07H 21/04; C07H 19/00

(52) U.S. Cl. .......................... 536/25.3; 435/6; 536/22.1; 536/23.1; 536/24.3; 536/25.31; 536/25.33; 536/25.34

(58) Field of Search ................................ 435/6; 536/22.1, 536/23.1, 24.3, 25.3, 25.31, 25.23, 25.34

(56) References Cited

U.S. PATENT DOCUMENTS

| | | | |
|---|---|---|---|
| 5,874,554 | 2/1999 | Gamble et al. | 536/22.1 |
| 5,908,926 | * 6/1999 | Pirrung et al. | 536/25.34 |

OTHER PUBLICATIONS

F. Baron et al. (1955), "Nucleotides. Pat XXXIII. The Structure of Cytidylic Acids a and b," *J. Chem. Soc.* 2855–2860.

J.F.M. deRooij et al. (1979), "Synthesis of Complementaty DNA Fragments via Phosphotriester Intermediates," *Recueuil, Journal of the Royal Netherlands Chemical Society* 98(11)537–548.

T. Fukuda et al. (1988), "Synthesis of RNA Oligomer Using 9–Fluorenylmethoxycarbonyl (Fmoc) Group for 5'–Hydroxyl Protection," *Nucleic Acids Research, Symposium Series* 19:13–16.

V. Haberman (1962), "The Degradatio of Apyrimidinic Deoxyribonucleic Acid in Alkali, A Method for the Isolation of Purine Nucleotide Sequences from Deoxyribonucleic Acid," *Biochim, Biophys. Acta* 55:999–1001.

S. Iwai et al. (1988), "5'–Levulinyl and 2'–Tetrahydrofuranyl Protection for the Synthesis of Oligoribonucleotides by the Phosphoramidite Approach," *Nucleic Acids Research* 16(20):9443–9456.

S. Iwai et al. (1988), "Synthesis of Oligoribonucleotides by the Phosphoramidite Approach Using 5'–Levulinyl and 2'–Tetrahydrofuranyl Protection," *Tetrahedron Letters* 29(42):5383–5386.

(List continued on next page.)

*Primary Examiner*—Jezia Riley

(57) ABSTRACT

The invention provides a method for synthesizing oligonucleotides using carbonate protection of hydroxyl groups and nucleophilic deprotection reagents. The deprotection reagents irreversibly cleave the carbonate protecting groups while simultaneously oxidizing the internucleotide phosphite triester linkage, and can be used in aqueous solution at neutral to mildly basic pH. The method eliminates the need for separate deprotection and oxidation steps, and, since the use of acid to remove protecting groups is unnecessary, acid-induced depurination is avoided. Fluorescent or other readily detectable carbonate protecting groups can be used, enabling monitoring of individual reaction steps during oligonucleotide synthesis. The invention is particularly useful in the highly parallel, microscale synthesis of oligonucleotides. Reagents and kits for carrying out the aforementioned method are provided as well.

39 Claims, 7 Drawing Sheets

OTHER PUBLICATIONS

Figure 1:
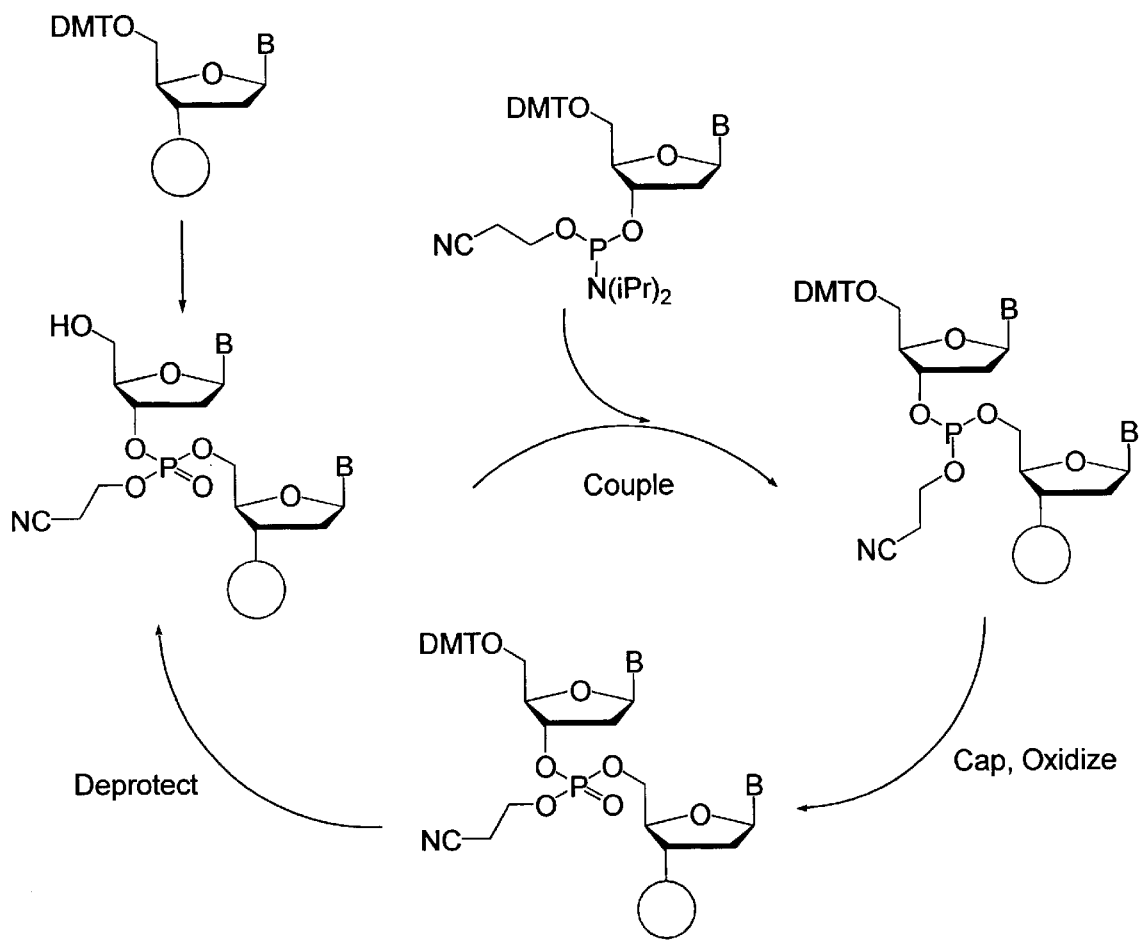

C. Lehmann et al. (1989), "Solid–Phase Synthesis of Oligoribonucleotides Using 9'–Fluorenylmethoxycarbonyl (Fmoc) for 5'–Hydroxyl Protection," *Nucleic Acids Research* 17(7):2379–2390.

R.L. Letsinger et al. (1967), "Oligonucleotide Syntheses Utilizingh β–Benzoylpropionyl, a Blocking Group with a Trigger for Selective Cleavage," *Journal of American Chemical Society* 89(26):7146–7147.

R.L. Letsinger et al. (1968), "Selective N–Debenzoylation of N,O–Polybenzoylnucleosides," *Tetrahedron Letters* 22:2621–2624.

H. Seliger et al. (1985), "The p–Phenylazophenyloxycarbonyl Protecting Group: Selective Deblocking and Oligonucleotide Synthesis Avoiding Acid Steps," *Nucleosides & Nucleotides* 4(1&2):153–155.

\* cited by examiner

3'-5' Synthesis With DMT Protection

◯ = Solid support/growing oligonucleotide

3'-5' Synthesis With Carbonate Protection

Comparison of Deprotection Mechanisms

5'-Arco-3'-Amidite Synthesis

B =
a A(N⁶-Bz)
b C(N⁴-Fmoc)
c G(N²-ibu)
d T

Arco =

(i) 4-Chlorophenyl chloroformate/pyridine/2 h;
(ii) (iPr$_2$N)$_2$PO(CH$_2$)$_2$CN/tetrazole/CH$_2$Cl$_2$/1 h.

5'-Arco-3'-Amidite Synthesis

B =
a A(N$^6$-Bz)
b C(N$^4$-Fmoc)
c G(N$^2$-ibu)
d T (i) 4-Chlorophenyl chloroformate/pyridine/2 h;
(ii) 3% Trichloroacetic acid/CH$_2$Cl$_2$/3 min;
(iii) (iPr$_2$N)$_2$PO(CH$_2$)$_2$CN/tetrazole/CH$_2$Cl$_2$/1 h.

SOLID PHASE SYNTHESIS OF OLIGONUCLEOTIDES USING CARBONATE PROTECTING GROUPS AND ALPHA-EFFECT NUCLEOPHILE DEPROTECTION

CROSS-REFERENCE TO RELATED APPLICATIONS

This is a continuation-in-part of U.S. patent application Ser. No. 09/128,052, filed Aug. 3, 1998, the disclosure of which is incorporated by reference herein.

TECHNICAL FIELD

The present invention relates generally to nucleic acid chemistry and to the chemical synthesis of oligonucleotides. More particularly, the invention relates to an improved method for synthesizing oligonucleotides wherein carbonates are used as hydroxyl-protecting groups and "alpha-effect" nucleophiles such as peroxides are used in the deprotection thereof. The invention has utility in the fields of biochemistry, molecular biology and pharmacology, and in medical diagnostic and screening technologies.

BACKGROUND

Solid phase chemical synthesis of DNA fragments is routinely performed using protected nucleoside phosphoramidites. S. L. Beaucage et al. (1981) Tetrahedron Lett. 22:1859. In this approach, the 3'-hydroxyl group of an initial 5'-protected nucleoside is first covalently attached to the polymer support. R. C. Pless et al. (1975) Nucleic Acids Res. 2:773 (1975). Synthesis of the oligonucleotide then proceeds by deprotection of the 5'-hydroxyl group of the attached nucleoside, followed by coupling of an incoming nucleoside-3'-phosphoramidite to the deprotected hydroxyl group. M. D. Matteucci et a. (1981) J. Am. Chem. Soc. 103:3185. The resulting phosphite triester is finally oxidized to a phosphorotriester to complete the internucleotide bond. R. L. Letsinger et al. (1976) J. Am. Chem. Soc. 9:3655. The steps of deprotection, coupling and oxidation are repeated until an oligonucleotide of the desired length and sequence is obtained. This process is illustrated schematically in FIG. 1 (wherein "B" represents a purine or pyrimidine base, "DMT" represents dimethoxytrityl and "iPR" represents isopropyl.

The chemical group conventionally used for the protection of nucleoside 5'-hydroxyls is dimethoxytrityl ("DMT"), which is removable with acid. H. G. Khorana (1968) Pure Appl. Chem. 17:349; M. Smith et al. (1962) J. Am. Chem. Soc. 84:430. This acid-labile protecting group provides a number of advantages for working with both nucleosides and oligonucleotides. For example, the DMT group can be introduced onto a nucleoside regioselectively and in high yield. E. I. Brown et al. (1979) Methods in Enzymol. 6:109. Also, the lipophilicity of the DMT group greatly increases the solubility of nucleosides in organic solvents, and the carbocation resulting from acidic deprotection gives a strong chromophore, which can be used to indirectly monitor coupling efficiency. M. D. Matteucci et al. (1980) Tetrahedron Lett. 21:719. In addition, the hydrophobicity of the group can be used to aid separation on reverse-phase HPLC. C. Becker et al. (1985) J. Chromatogr. 326:219.

However, use of DMT as a hydroxyl-protecting group in oligonucleotide synthesis is also problematic. The N-glycosidic linkages of oligodeoxyribonucleotides are susceptible to acid catalyzed cleavage (N. K. Kochetkov et al., Organic Chemistry of Nucleic Acids (New York: Plenum Press, 1972)), and even when the protocol is optimized, recurrent removal of the DMT group with acid during oligonucleotide synthesis results in depurination. H. Shaller et al. (1963) J. Am. Chem. Soc. 8:3821. The N-6-benzoyl-protected deoxyadenosine nucleotide is especially susceptible to glycosidic cleavage, resulting in a substantially reduced yield of the final oligonucleotide. J. W. Efcavitch et al. (1985) Nucleosides & Nucleotides 4:267. Attempts have been made to address the problem of acid-catalyzed depurination utilizing alternative mixtures of acids and various solvents; see, for example, E. Sonveaux (1986) Bioorganic Chem. 4:274. However, this approach has met with limited success. L. J. McBride et al. (1986) J. Am. Chem. Soc. 108:2040.

Conventional synthesis of oligonucleotides using DMT as a protecting group is problematic in other ways as well. For example, cleavage of the DMT group under acidic conditions gives rise to the resonance-stabilized and long-lived bis(p-anisyl)phenylmethyl carbocation. P. T. Gilham et al. (1959) J. Am. Chem. Soc. 81:4647. Protection and deprotection of hydroxyl groups with DMT are thus readily reversible reactions, resulting in side reactions during oligonucleotide synthesis and a lower yield than might otherwise be obtained. To circumvent such problems, large excesses of acid are used with DMT to achieve quantitative deprotection. As bed volume of the polymer is increased in larger scale synthesis, increasingly greater quantities of acid are required. The acid-catalyzed depurination which occurs during the synthesis of oligodeoxyribonucleotides is thus increased by the scale of synthesis. M. H. Caruthers et al., in Genetic Engineering: Principles and Methods, J. K. Setlow et al., Eds. (New York: Plenum Press, 1982).

Considerable effort has been directed to developing 5'-O-protecting groups which can be removed under non-acidic conditions. For example, R. L. Letsinger et al. (1967) J. Am. Chem. Soc. 89:7147, describe use of a hydrazine-labile benzoyl-propionyl group, and J. F. M. deRooij et al. (1979) Real. Track. Chain. Pays-Bas. 9:537, describe using the hydrazine-labile levulinyl ester for 5'-OH protection (see also S. Iwai et al. (1988) Tetrahedron Lett. 22:5383; and S. Iwai et al. (1988) Nucleic Acids Res. 16:9443). However, the cross-reactivity of hydrazine with pyrimidine nucleotides (as described in F. Baron et al. (1955) J. Chem. Soc. 2855 and in V. Habermann (1962) Biochem. Biophys. Acta 55:999), the poor selectivity of levulinic anhydride and hydrazine cleavage of N-acyl protecting groups (R. L. Letsinger et al. (1968), Tetrahedron Lett. 22:2621) have made these approaches impractical. H. Seliger et al. (1985), Nucleosides & Nucleotides 4:153, describes the 5'-O-phenyl-azophenyl carbonyl ("PAPco") group, which is removed by a two-step procedure involving transesterification followed by β-elimination; however, unexpectedly low and non-reproducible yields resulted. Fukuda et al. (1988) Nucleic Acids Res. Symposium Ser.19, 13, and C. Lehmann et al. (1989) Nucleic Acids Res. 17:2389, describe application of the 9-fluorenylmethylcarbonate ("Fmoc") group for 5'-protection. C. Lehmann et al. (1989) report reasonable yields for the synthesis of oligonucleotides up to 20 nucleotides in length. The basic conditions required for complete deprotection of the Fmoc group, however, lead to problems with protecting group compatibility. Similarly, R. L. Letsinger et al. (1967), J. Am. Chem. Soc. 32:296, describe using the p-nitrophenyloxycarbonyl group for 5'-hydroxyl protection. In all of the procedures described above utilizing base-labile 5'-O-protecting groups, the requirements of high basicity and long deprotection times have severely limited their application for routine synthesis of oligonucleotides.

Still an additional drawback associated with conventional oligonucleotide synthesis using DMT as a hydroxyl-protecting group is the necessity of multiple steps, particularly the post-synthetic deprotection step in which the DMT group is removed following oxidation of the internucleotide phosphite triester linkage to a phosphorotriester. It would be desirable to work with a hydroxyl-protecting group that could be removed via oxidation, such that the final two steps involved in nucleotide addition, namely oxidation and deprotection, could be combined.

The problems associated with the use of DMT are exacerbated in solid phase oligonucleotide synthesis where "microscale" parallel reactions are taking place on a very dense, packed surface. Applications in the field of genomics and high throughput screening have fueled the demand for precise chemistry in such a context. Thus, increasingly stringent demands are placed on the chemical synthesis cycle as it was originally conceived, and the problems associated with conventional methods for synthesizing oligonucleotides are rising to unacceptable levels in these expanded applications.

The invention is thus addressed to the aforementioned deficiencies in the art, and provides a novel method for synthesizing oligonucleotides, wherein the method has numerous advantages relative to prior methods such as those discussed above. The novel method involves the use of neutral or mildly basic conditions to remove hydroxyl-protecting groups, such that acid-induced depurination is avoided. In addition, the reagents used provide for irreversible deprotection, significantly reducing the likelihood of unwanted side reactions and increasing the overall yield of the desired product. The method provides for simultaneous oxidation of the internucleoside phosphite triester linkage and removal of the hydroxyl-protecting group, eliminating the extra step present in conventional processes for synthesizing oligonucleotides; the method also avoids the extra step of removing exocyclic amine protecting groups, as the reagents used for hydroxyl group deprotection substantially remove exocyclic amine protecting groups. In addition, the method can be used in connection with fluorescent or other readily detectable protecting groups, enabling monitoring of individual reaction steps. Further, the method is useful in carrying out either 3'-to-5' synthesis or 5'-to-3' synthesis. Finally, because of the far more precise chemistry enabled by the present invention, the method readily lends itself to the highly parallel, microscale synthesis of oligonucleotides.

SUMMARY OF THE INVENTION

It is accordingly a primary object of the invention to provide a novel method for synthesizing oligonucleotides which addresses and overcomes the above-mentioned disadvantages of the prior art.

It is another object of the invention to provide a novel method for synthesizing oligonucleotides in which individual nucleoside monomers are added to a growing oligonucleotide chain using carbonates as hydroxyl-protecting groups and "alpha effect" nucleophiles as deprotecting reagents.

It is still another object of the invention to provide such a method in which hydroxyl group deprotection and oxidation of the internucleotide phosphite triester linkage are carried out simultaneously, in a single step.

It is yet another object of the invention to provide such a method in which deprotection and oxidation are conducted in aqueous solution at neutral or mildly basic pH.

It is an additional object of the invention to provide such a method in which removal of hydroxyl protecting groups during oligonucleotide synthesis is irreversible.

It is a further object of the invention to provide such a method in which the desired oligonucleotide can be synthesized in either the 3'-to-5' direction or the 5'-to-3' direction.

Still a further object of the invention is to provide such a method in which individual oligonucleotides are synthesized within the context of a highly dense, substantially parallel oligonucleotide array on a substrate surface.

Still an additional object of the invention is to provide nucleoside reagents useful in conjunction with the novel synthetic methods.

Additional objects, advantages and novel features of the invention will be set forth in part in the description which follows, and in part will become apparent to those skilled in the art upon examination of the following, or may be learned by practice of the invention.

The invention is premised on the discovery that rapid and selective removal of suitable 5'-OH or 3'-OH protecting groups following phosphoramidite condensation can be achieved by employing nucleophiles, and particularly peroxy anions, that exhibit an "alpha effect" under neutral or mildly basic conditions. Further, it has now been discovered that rapid and selective deprotection can be achieved under such conditions by employing carbonate groups for 5'-OH or 3'-OH protection. Deprotection of nucleoside carbonates using peroxy anions can be conducted in aqueous solution, at neutral or mild pH, resulting in quantitative removal of the carbonate group and concomitant and quantitative oxidation of the internucleotide phosphite triester bond. Oligonucleotides synthesized using the novel methodology can be isolated in high yield and substantially free of detectable nucleoside modifications.

The term "alpha effect," as in an "alpha effect" nucleophilic deprotection reagent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Brønsted-type nucleophilicity plot. S. Hoz et al. (1985) *Israel J. Chem.* 26:313. See also, J. D. Aubort et al. (1970) *Chem. Comm.* 1378; J. M. Brown et al. (1979) *J. Chem. Soc. Chem. Comm.* 171; E. Buncel et al.(1982) *J. Am. Chem. Soc.* 104:4896; J. O. Edwards et al. (1962) *J. Amer. Chem. Soc.* 84:16; J. D. Evanseck et al. (1987) *J. Am. Chem Soc.* 109:2349. The magnitude of the alpha effect is dependent upon the electrophile which is paired with the specific nucleophile. J. E. Mclsaac, Jr. et al. (1972), *J. Org. Chem.* 31:1037. Peroxy anions are example of nucleophiles which exhibit strong alpha effects.

In one general aspect, the invention features a method, in an oligonucleotide synthesis, for removing a protecting group from a protected nucleoside, by reacting the protected nucleoside or protected nucleotide with a nucleophile that exhibits an alpha effect at conditions of mildly basic pH, and particularly at conditions of pH 10 or less.

The invention provides for efficient solid-phase synthesis of oligonucleotides of lengths up to 25 nucleotides and greater. Treatment using an alpha effect nucleophile according to the invention for removal of carbonate protecting groups is irreversible, resulting in breakdown of the carbonate and formation of $CO_2$. Moreover, because such treatment results in concomitant oxidation of the internucleotide bond and substantial removal of exocyclic amine protecting groups, the method of the invention obviates the need for a separate oxidation step and a postsynthesis deprotection step to remove any exocyclic amine protecting groups that may be used.

In another general aspect, the invention features a method for making an oligonucleotide array made up of array features each presenting a specified oligonucleotide sequence at an address on an array substrate, by first treating the array substrate to protect the hydroxyl moieties on the derivatized surface from reaction with phosphoramidites, then carrying out the steps of (a) applying droplets of an alpha effect nucleophile to effect deprotection of hydroxyl moieties at selected addresses, and (b) flooding the array substrate with a medium containing a selected protected phosphoramidite to permit coupling of the selected phosphoramidite onto the deprotected hydroxyl moieties at the selected addresses, and repeating the steps (a) and (b) to initiate and to sequentially build up oligonucleotides having the desired sequences at the selected addresses to complete the array features. In a variation on the aforementioned method, the droplets applied may comprise the protected phosphoramidite, and the alpha effect nucleophile may be used to flood the array substrate.

In the array construction method according to the invention, the deprotection reagents are aqueous, allowing for good droplet formation on a wide variety of array substrate surfaces. Moreover, because the selection of features employs aqueous media, small-scale discrete droplet application onto specified array addresses can be carried out by adaptation of techniques for reproducible fine droplet deposition from printing technologies. Further, as noted above, the synthesis reaction provides irreversible deprotection resulting in evolution of $CO_2$, and thus quantitative removal of protecting groups within each droplet may be achieved. The phosphoramidite reactions are carried out in bulk, employing an excess of the phosphoramidite during the coupling step (b), allowing for exclusion of water by action of the excess phosphoramidite as a desiccant.

DETAILED DESCRIPTION OF THE FIGURES

FIG. 1 schematically illustrates conventional 3'-to-5' oligonucleotide synthesis using DMT as a 5'-OH protecting group, and separate deprotection and oxidation steps.

Figure 2:
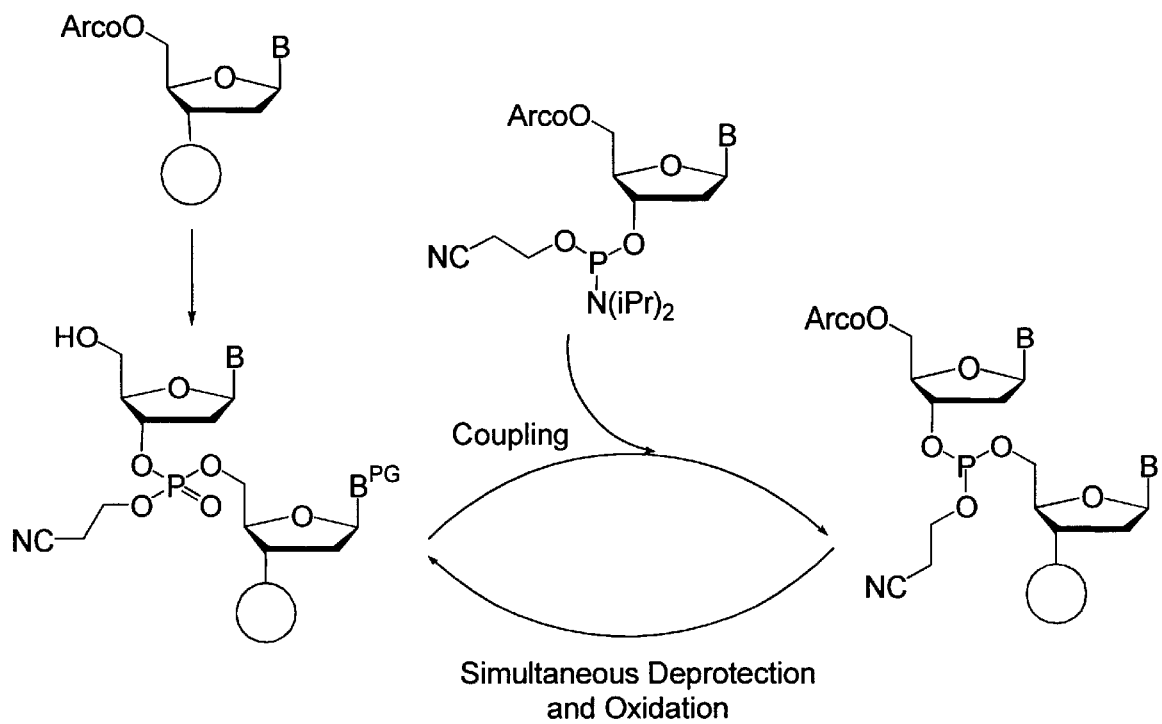
Figure 2:
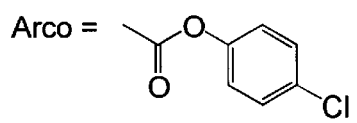

FIG. 2 schematically illustrates 3'-to-5' oligonucleotide synthesis using the method of the invention.

Figure 3A:
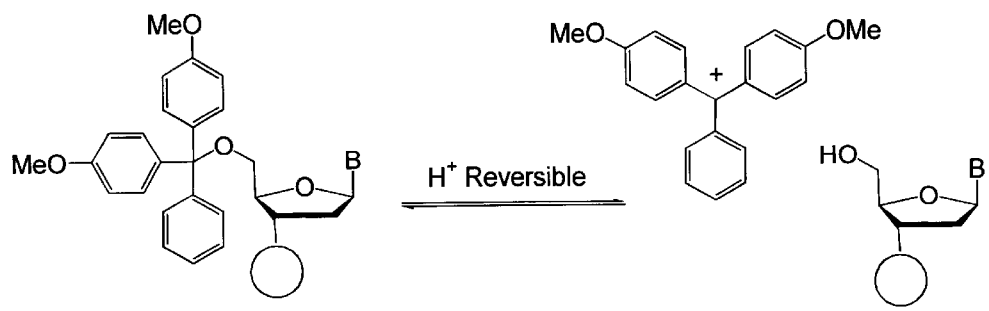
Figure 3B:
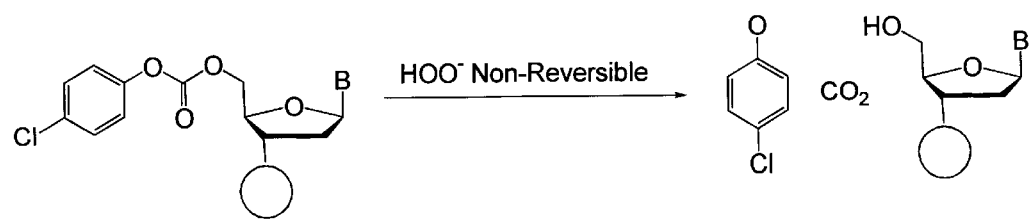

FIGS. 3A and 3B compare the conventional deprotection reaction in which DMT is used as a hydroxyl-protecting group (FIG. 3A) and the deprotection reaction in which the reagents of the invention are employed (FIG. 3B).

Figure 4:
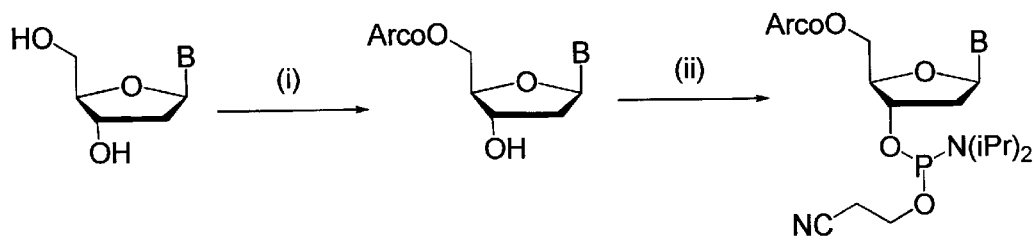
Figure 4:
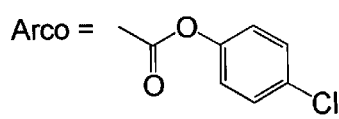

FIG. 4 schematically illustrates a method for synthesizing a 5'-carbonate-3'-phosphoramidite monomer of the invention.

Figure 5:
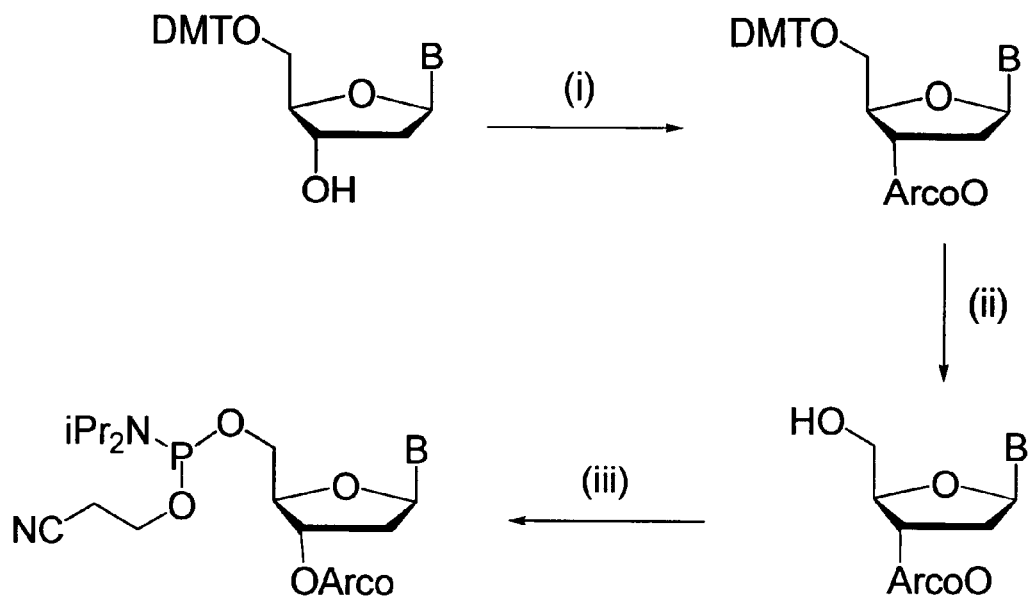

FIG. 5 schematically illustrates a method for synthesizing a 3'-carbonate-5'-phosphoramidite monomer of the invention.

Figure 6:
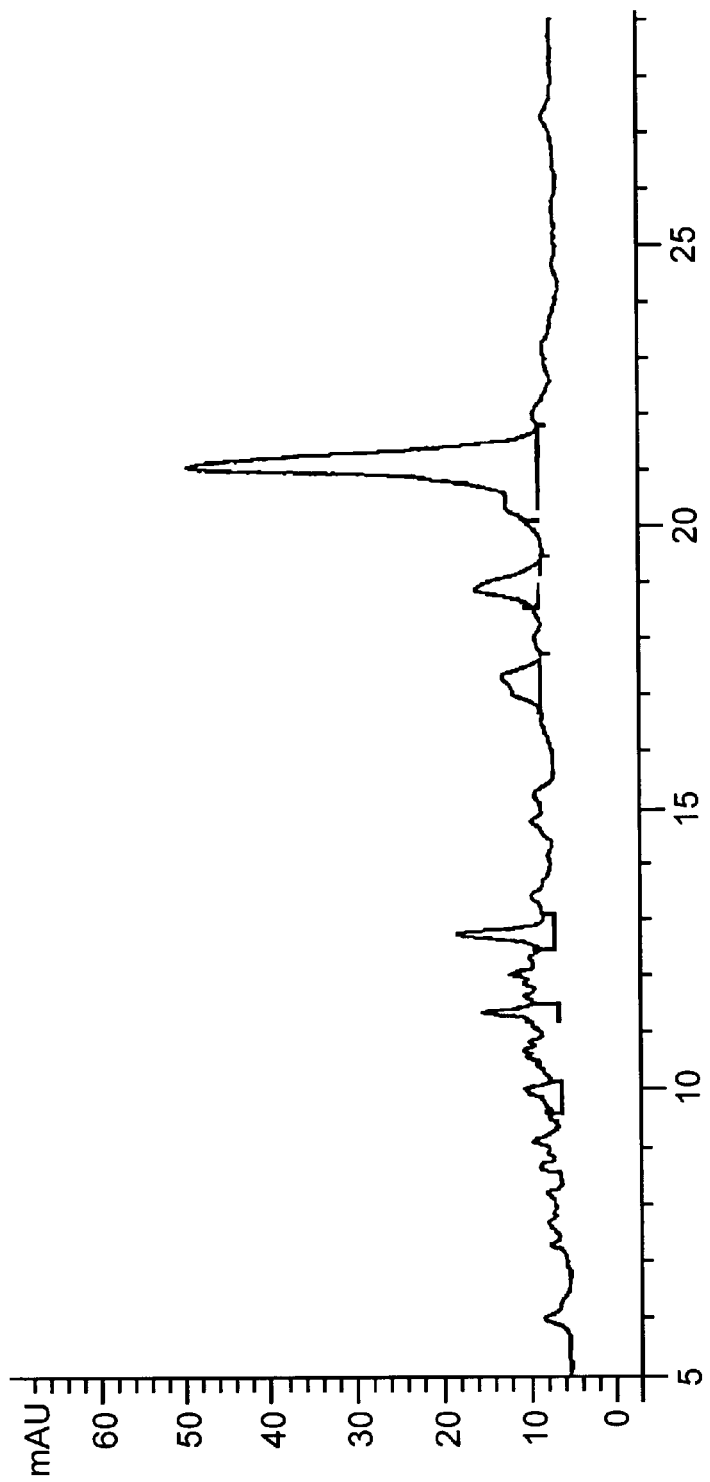

FIG. 6 sets forth the HPLC results obtained for a mixed-sequence oligonucleotide synthesized in Example 4, part (D).

Figure 7:
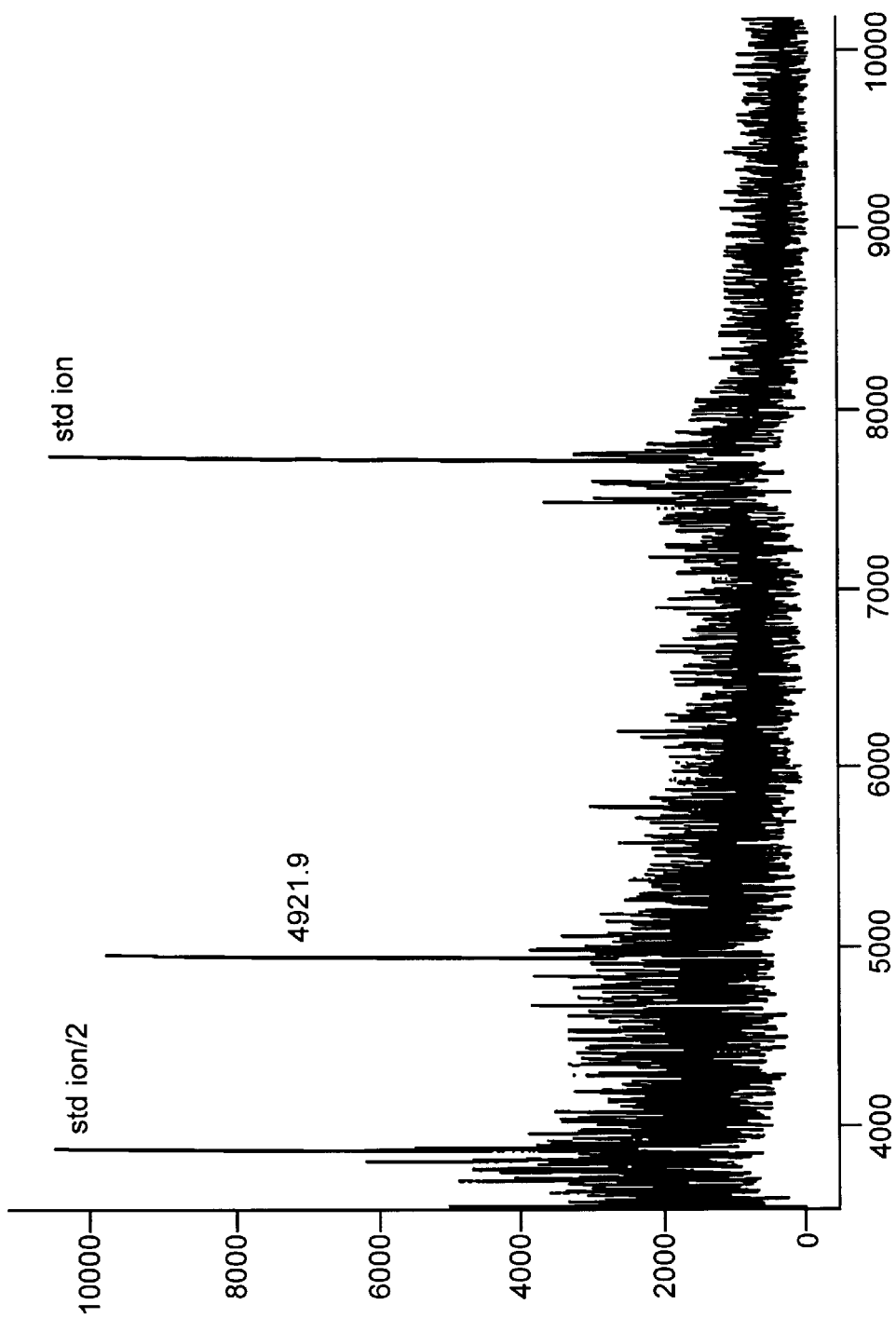

FIG. 7 sets forth the MALDI TOF results obtained for the same mixed-sequence oligonucleotide.

DETAILED DESCRIPTION OF THE INVENTION

DEFINITIONS AND NOMENCLATURE:

It is to be understood that unless otherwise indicated, this invention is not limited to specific reagents, reaction conditions, synthetic steps, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a protecting group" includes combinations of protecting groups, reference to "a nucleoside" includes combinations of nucleosides, and the like. Similarly, reference to "a substituent" as in a compound substituted with "a substituent" includes the possibility of substitution with more than one substituent, wherein the substituents may be the same or different.

In this specification and in the claims which follow, reference will be made to a number of terms which shall be defined to have the following meanings:

The term "alkyl" as used herein, unless otherwise specified, refers to a saturated straight chain, branched or cyclic hydrocarbon group of 1 to 24, typically 1–12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "alkenyl" as used herein, unless otherwise specified, refers to a branched, unbranched or cyclic (in the case of $C_5$ and $C_6$) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of amino, halogen and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure $—(CH_2)_j—Ar$ wherein j is an integer in the range of 1 to 24, more typically 1 to 6, and Ar is a monocyclic aryl moiety.

The term "electron withdrawing" denotes the tendency of a substituent to attract valence electrons of the molecule of which it is a part, i.e., an electron-withdrawing substituent is electronegative.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocyclic groups include piperidinyl, morpholinyl and pyrrolidinyl.

The term "halo" or "halogen" is used in its conventional sense to refer to a chloro, bromo, fluoro or iodo substituent.

As used herein, the term "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones, providing that the polymers contain nucleobases in a configuration which allows for base pairing and base stacking, such as is found in DNA and RNA.

It will be appreciated that, as used herein, the terms "nucleoside" and "nucleotide" will include those moieties which contain not only the known purine and pyrimidine bases, but also modified purine and pyrimidine bases and other heterocyclic bases which have been modified (these moieties are sometimes referred to herein, collectively, as "purine and pyrimidine bases and analogs thereof"). Such modifications include methylated purines or pyrimidines, acylated purines or pyrimidines, and the like.

By "protecting group" as used herein is meant a species which prevents a segment of a molecule from undergoing a specific chemical reaction, but which is removable from the molecule following completion of that reaction. This is in contrast to a "capping group," which permanently binds to a segment of a molecule to prevent any further chemical transformation of that segment.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

OLIGONUCLEOTIDE SYNTHESIS USING CARBONATE PROTECTION AND IRREVERSIBLE NUCLEOPHILIC DEPROTECTION:

In a first embodiment, the invention pertains to a method for synthesizing an oligonucleotide on a solid support, wherein a carbonate is used as a hydroxyl-protecting group and an alpha effect nucleophile is used to bring about deprotection. The novel synthesis is based on a simple, two-step method of (1) coupling a hydroxyl-protected nucleoside monomer to a growing oligonucleotide chain, and (2) deprotecting the product, under neutral or mildly basic conditions, using an alpha effect nucleophilic reagent that also oxidizes the internucleotide linkage to give a phosphotriester bond. The coupling and deprotection/oxidation steps are repeated as necessary to give an oligonucleotide having a desired sequence and length.

In the initial step of the synthesis, then, an unprotected nucleoside is covalently attached to a solid support to serve as the starting point for oligonucleotide synthesis. The nucleoside may be bound to the support through its 3'-hydroxyl group or its 5'-hydroxyl group, but is typically bound through the 3'-hydroxyl group. A second nucleoside monomer is then coupled to the free hydroxyl group of the support-bound initial monomer, wherein for 3'-to-5' oligonucleotide synthesis, the second nucleoside monomer has a phosphorus derivative such as a phosphoramidite at the 3' position and a carbonate protecting group at the 5' position, and alternatively, for 5'-to-3' oligonucleotide synthesis, the second nucleoside monomer has a phosphorus derivative at the 5' position and a carbonate protecting group at the 3' position. This coupling reaction gives rise to a newly formed phosphite triester bond between the initial nucleoside monomer and the added monomer, with the carbonate-protected hydroxyl group intact. In the second step of the synthesis, the carbonate group is removed with an alpha effect nucleophile that also serves to oxidize the phosphite triester linkage to the desired phosphotriester.

More specifically, for 3'-to-5' synthesis, a support-bound nucleoside monomer is provided having the structure (I)

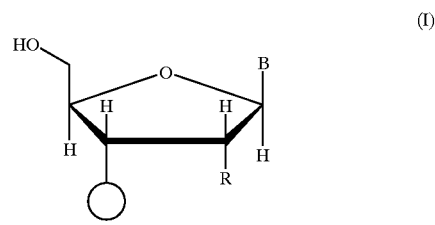

(I)

wherein:
○ represents the solid support or a support-bound oligonucleotide chain;

R is hydrido or hydroxyl, wherein when R is hydrido, the support-bound nucleoside is a deoxyribonucleoside, as will be present in DNA synthesis, and when R is hydroxyl, the support-bound nucleoside is a ribonucleoside, as will be present in RNA synthesis; and B is a purine or pyrimidine base. The purine or pyrimidine base may be conventional, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil- 5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The protected monomer to be added has the structure of formula (II)

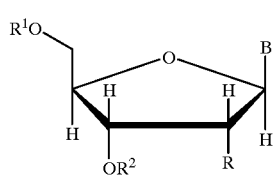

(II)

in which B and R are as defined above with respect to the support-bound nucleoside of structural formula (I), and $R^1$ is $COOR^3$, such that a carbonate group —$OCOOR^3$ is present at the 5' position. $R^3$ is generally substituted or unsubstituted hydrocarbyl, including alkyl, aryl, aralkyl, alkaryl, cycloalkyl, alkenyl, cycloalkenyl, alkynyl, cycloalkynyl, optionally containing one or more nonhydrocarbyl linkages such as ether linkages, thioether linkages, oxo linkages, amine and imine linkages, and optionally substituted on one or more available carbon atoms with a nonhydrocarbyl substituent such as cyano, nitro, halo, or the like. Preferred carbonate groups —$OCOOR^3$ are aryl carbonates, i.e., $R^3$ is aryl. Suitable aryl carbonates include, for example, o-nitrophenylcarbonyl, p-phenylazophenylcarbonyl, phenylcarbonyl, p-chlorophenylcarbonyl, 5'-(α-methyl-2-nitropiperonyl)oxycarbonyl ("MeNPOC"), and 9-fluorenylmethylcarbonyl ("Fmoc"). Particularly preferred aryl carbonates have the structure Ar-L—O—(CO)—O— wherein Ar is an aromatic moiety, typically a monocyclic aromatic moiety such as a phenyl group, optionally substituted with one or more electron-withdrawing substituents such as halo, nitro, cyano, or the like, and L is a lower alkylene linkage. Preferred alkyl carbonate substituents are fluorinated alkyl carbonates such as 2,2,2-trichloro-1,1-dimethylcarbonyl ("TCBOC") and cyano-substituted alkyl carbonates such as 1,1-dimethyl-2-cyanoethyl carbonate

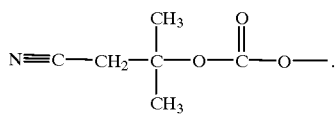

$R^3$ may also be a fluorescent or colored moiety. Preferably, in this embodiment, $R^3$ becomes fluorescent or colored upon cleavage of the carbonate —$OCOOR^3$, but is neither fluorescent nor colored when bound to the nucleoside in carbonate form. In this way, when the carbonate protecting group $R^1$ is removed, the reaction may be monitored by detecting a fluorescent or colored cleavage product. Alternatively, $R^3$ may be fluorescent or colored when bound to the nucleoside in carbonate form, such that the presence of the newly attached monomer can be immediately detected. Examples of fluorescent and colorimetric species that may be employed include, but are not limited to: xanthenes such as fluoresceins, eosins and erythrosins, with preferred fluorescein compounds exemplified by 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein; rhodamines such as tetramethylrhodamine and Texas Red®; benzimidazoles; ethidiums; propidiums; anthracyclines; mithramycins; acridines; actinomycins; merocyanines; coumarins such as 4-methyl-7-methoxycoumarin; pyrenes; chrysenes; stilbenes; anthracenes; naphthalenes such as dansyl, 5-dimethylamino- 1-naphthalenesulfonyl; salicylic acids; benz-2-oxa-1-diazoles (also known as benzofurans), including 4-amino-7-nitrobenz-2-oxa-1,3-diazole; fluorescamine; and 4-methylumbelliferone.

$R^2$ is a phosphorus derivative that enables coupling to a free hydroxyl group. Preferred phosphorus derivatives are phosphoramidites, such that $R^2$ has the structure (III)

(III)

wherein X is $NQ^1Q^2$ in which $Q^1$ and $Q^2$ may be the same or different and are typically selected from the group consisting of alkyl, aryl, aralkyl, alkaryl, cycloalkyl, alkenyl, cycloalkenyl, alkynyl, cycloalkynyl, optionally containing one or more nonhydrocarbyl linkages such as ether linkages, thioether linkages, oxo linkages, amine and imine linkages, and optionally substituted on one or more available carbon atoms with a nonhydrocarbyl substituent such as cyano, nitro, halo, or the like. Preferably, $Q^1$ and $Q^2$ represent lower alkyl, more preferably sterically hindered lower alkyls such as isopropyl, t-butyl, isobutyl, sec-butyl, neopentyl, tert-pentyl, isopentyl, sec-pentyl, and the like. Most preferably, $Q^1$ and $Q^2$ both represent isopropyl. Alternatively, $Q^1$ and $Q^2$ may be linked to form a mono- or polyheterocyclic ring having a total of from 1 to 3, usually 1 to 2 heteroatoms and from 1 to 3 rings. In such a case, $Q^1$ and $Q^2$ together with the nitrogen atom to which they are attached represent, for example, pyrrolidone, morpholino or piperidino. Usually, $Q^1$ and $Q^2$ have a total of from 2 to 12 carbon atoms. Examples of specific —$NQ^1Q^2$ moieties thus include, but are not limited to, dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine, and the like.

The moiety "Y" is hydrido or hydrocarbyl, typically alkyl, alkenyl, aryl, aralkyl, or cycloalkyl. Preferably, Y represents: lower alkyl; electron-withdrawing β-substituted aliphatic, particularly electron-withdrawing β-substituted ethyl such as β-trihalomethyl ethyl, β-cyanoethyl, β-sulfoethyl, β-nitro-substituted ethyl, and the like; electron-withdrawing substituted phenyl, particularly halo-, sulfo-, cyano- or nitro-substituted phenyl; or electron-withdrawing substituted phenylethyl. Most preferably, Y represents methyl, β-cyanoethyl, or 4-nitrophenylethyl.

The coupling reaction is conducted under standard conditions used for the synthesis of oligonucleotides and conventionally employed with automated oligonucleotide synthesizers. Such methodology will be known to those skilled in the art and is described in the pertinent texts and literature, e.g., in D. M. Matteuci et al. (1980) *Tet. Lett.* 521:719 and U.S. Pat. No. 4,500,707. The product of the coupling reaction may be represented as structural formula (IV), as follows:

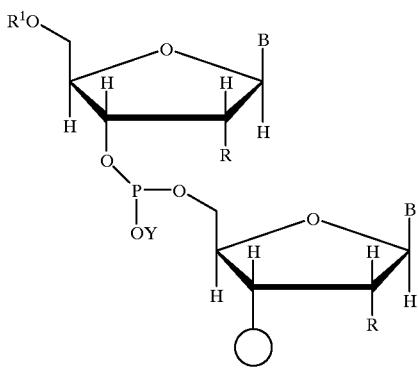

(IV)

In the second step of the synthesis, the product (IV) is treated with an "alpha effect" nucleophile in order to remove the carbonate protecting group at the 5' terminus, thus converting the moiety —OR$^1$ to —OH. The alpha effect nucleophile also oxidizes the newly formed phosphite triester linkage —O—P(OY)—O— to give the desired phosphotriester linkage

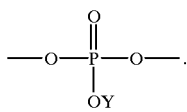

Advantageously, this step is conducted in an aqueous solution at neutral pH or at a mildly basic pH, depending on the pKa of the nucleophilic deprotection reagent. That is, and as will be explained in further detail below, the pH at which the deprotection reaction is conducted must be above the pKa of the deprotection reagent for the reagent to be effective. Typically, the reaction is conducted at a pH of less than about 10.

In a preferred embodiment, the nucleophilic deprotection reagent that exhibits an alpha effect is a peroxide or a mixture of peroxides, and the pH at which deprotection is conducted is at or above the pKa for formation of the corresponding peroxy anion. The peroxide may be either inorganic or organic. Suitable inorganic peroxides include those of the formula M$^+$OOH$^-$, where M is any counteranion, including for example H$^+$, Li$^+$, Na$^+$, K$^+$, Rb$^+$, Cs$^+$, or the like; and lithium peroxide or hydrogen peroxide can be particularly suitable. Suitable organic peroxides include those of the formula ROOH, where R is selected from the group consisting of alkyl, aryl, substituted alkyl and substituted aryl. More particularly, the organic peroxide will have one of the following three general structures (V), (VI) or (VII)

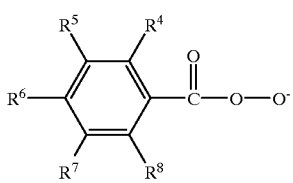

(V)

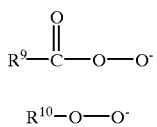

(VI)

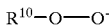

(VII)

in which R$^4$ through R$^{10}$ are generally hydrocarbyl optionally substituted with one or more nonhydrocarbyl substituents and optionally containing one or more nonhydrocarbyl linkages. Generally, R$^4$ through R$^{10}$ are independently selected from the group consisting of hydrido, alkyl, aryl, aralkyl, cycloalkyl, cycloalkylalkyl, alkenyl, cycloalkenyl, alkynyl aralkynyl, cycloalkynyl, substituted aralkyl, substituted cycloalkyl, substituted cycloalkylalkyl, substituted alkenyl, substituted cycloalkenyl, substituted alkynyl substituted aralkynyl, substituted cycloalkynyl; t-butyl-hydroperoxide or metachloroperoxybenzoic acid can be particularly suitable. As a specific example, the m-chloroperbenzoic acid (mCPBA) peroxy anion exhibits a strong alpha effect towards the p-chlorophenylcarbonate electrophile, and that, accordingly, the peroxyanion of mCPBA is a particularly effective deprotection reagent for removal of p-chlorophenylcarbonate protecting groups.

The product of this simultaneous deprotection and oxidation step may thus be represented as follows:

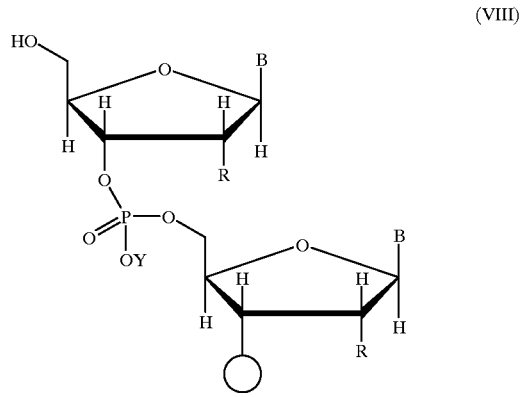

(VIII)

wherein B, R and Y are as defined earlier herein. This latter reaction also gives rise to the by-products R$^3$O$^-$ and carbon dioxide, insofar as nucleophilic attack of the peroxide deprotection reagent cleaves the carbonate linkage as follows:

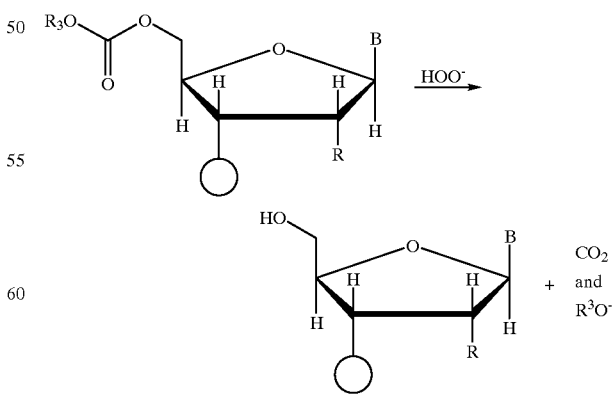

The use of a peroxy anion to effect simultaneous removal of the carbonate protecting group and oxidation of the intemucleotide linkage also removes, to a large extent, exocyclic amine-rotecting groups such as acetyl, trifluoroacetyl, difluoroacetyl and trifluoroacetyl moieties. Thus, an added advantage herein is the elimination of a separate post-synthetic reaction step to remove exocyclic amine-protecting groups, as is required with conventional methods of synthesizing oligonucleotides. Elimination of this additional step significantly decreases the time and complexity involved in oligonucleotide synthesis.

An additional advantage of peroxy anions as deprotection reagents herein is that they may be readily activated or inactivated by simply changing pH. That is, the effectiveness of peroxides as nucleophiles is determined by their pKa. In buffered solutions having a pH below the pKa of a particular peroxide, the peroxides are not ionized and thus are non-nucleophilic. To activate a peroxide and render it useful as a deprotection reagent for use herein, the pH is increased above the pKa so that the peroxide is converted to a nucleophilic peroxy anion. Thus, one can carefully control the timing and extent of the deprotection reaction by varying the pH of the peroxide solution used.

FIG. 2 schematically illustrates 3'-to-5' synthesis of an oligonucleotide using the method of the present invention. In the figure, the moiety "Arco" ("aryloxycarbonyl") represents the carbonate protecting group p-chlorophenylcarbonyl. As may be seen, deprotection and oxidation occur simultaneously. The synthesis may be contrasted with that schematically illustrated in FIG. 1, the prior, conventional method employing DMT protection and separate oxidation and deprotection steps. A further advantage of the invention is illustrated in FIG. 3. As shown therein, in FIG. 3A, protection and deprotection of hydroxyl groups using DMT is a reversible process, with the DMT cation shown being a relatively stable species. Thus, using DMT as a protecting group can lead to poor yields and unwanted side reactions, insofar as the deprotection reaction is essentially reversible. FIG. 3B illustrates the irreversible deprotection reaction of the present invention, wherein nucleophilic attack of the peroxy anion irreversibly cleaves the carbonate moiety, i.e., the O-p-chlorophenylcarbonyl group, giving rise to carbon dioxide and the p-chlorophenol anion. The reaction is not "reversible," insofar as there is no equilibrium reaction in which a cleaved protecting group could reattach to the hydroxyl moiety, as is the case with removal of DMT.

As explained earlier herein, the method of the invention also lends itself to synthesis in the 5'-to-3' direction. In such a case, the initial step of the synthetic process involves attachment of a nucleoside monomer to a solid support at the 5' position, leaving the 3' position available for covalent binding of a subsequent monomer. In this embodiment, i.e., for 5'-to-3' synthesis, a support-bound nucleoside monomer is provided having the structure (IX)

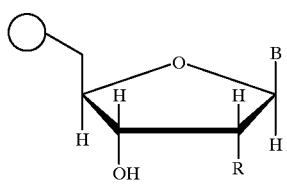
(IX)

wherein ○ represents the solid support or a support-bound oligonucleotide chain, R is hydrido or hydroxyl, and B is a purine or pyrimidine base. The protected monomer to be added has the structure of formula (X)

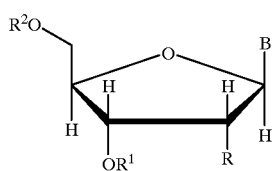
(X)

wherein the carbonate protecting group is present at the 3' position, i.e., $R^1$ is $COOR^3$ where $R^3$ is as defined previously, and $R^2$ represents a phosphorus derivative that enables coupling to a free hydroxyl group, preferably a phosphoramidite having the structure (III)

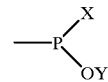
(III)

wherein X and Y are as defined earlier herein. The coupling reaction in which the nucleoside monomer becomes covalently attached to the 3' hydroxyl moiety of the support bound nucleoside is conducted under reaction conditions identical to those described for the 3'-to-5' synthesis. This step of the synthesis gives rise to the intermediate (XI)

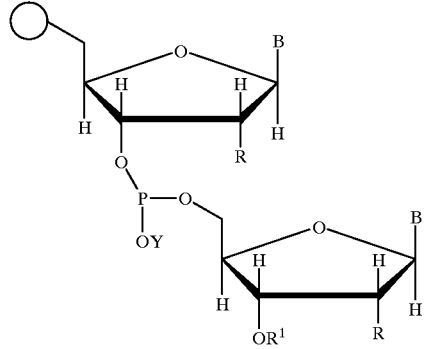
(XI)

As described with respect to oligonucleotide synthesis in the 3'-to-5' direction, the coupling reaction is followed by treatment of the product (XI) with an alpha effect nucleophile in order to remove the carbonate protecting group at the 3' terminus, thus converting the moiety —$OR^1$ to —OH, and to oxidize the internucleotide phosphite triester linkage to give the desired phosphotriester linkage.

The two-step process of coupling and deprotection/oxidation is repeated until the oligonucleotide having the desired sequence and length is obtained. Following synthesis, the oligonucleotide may, if desired, be cleaved from the solid support.

The synthetic methods of the invention may be conducted on any solid substrate having a surface to which chemical entities may bind. Suitable solid supports are typically polymeric, and may have a variety of forms and compositions and derive from naturally occurring materials, naturally occurring materials that have been synthetically modified, or synthetic materials. Examples of suitable support materials include, but are not limited to, polysaccharides such as agarose (e.g., that available commercially as Sepharosee®, from Pharmacia) and dextran (e.g., those available commercially under the tradenames Sephadex® and Sephacyle®, also from Pharmacia), polyacrylamides, polystyrenes, polyvinyl alcohols, copolymers of hydroxyethyl methacrylate and methyl methacrylate, silicas, teflons, glasses, and the like. The initial monomer of the oligonucleotide to be synthesized on the substrate surface is typically bound to a linking moiety which is in turn bound to a surface hydrophilic group, e.g., to a surface hydroxyl moiety present on a silica substrate.

SYNTHESIS OF OLIGONUCLEOTIDE ARRAYS:

In a related embodiment, the invention features a method for making an oligonucleotide array made up of array features each presenting a specified oligonucleotide sequence at an address on an array substrate. First, the array substrate is treated to protect the hydroxyl moieties on the derivatized surface from reaction with phosphoramidites or analogous phosphorus groups used in oligonucleotide synthesis. Protection involves conversion of free hydroxyl groups to —OR$^1$ groups, i.e., to carbonate-protected species. The method then involves (a) applying droplets of an alpha effect nucleophile to effect deprotection of hydroxyl moieties at selected addresses and oxidation of the newly formed internucleotide phosphite triester linkages, followed by (b) flooding the array substrate with a medium containing a selected nucleoside monomer having the structure of either Formula (II) (for 3'-to-5' synthesis) or Formula (X) (for 5'-to-3' synthesis). Step (a), deprotection/oxidation, and step (b), monomer addition, are repeated to sequentially build oligonucleotides having the desired sequences at selected addresses to complete the array features. In a variation on the aforementioned method, the applied droplets may comprise the selected nucleoside monomer, while the alpha effect nucleophile is used to flood the array substrate; that is, steps (a) and (b) are essentially reversed.

In the array construction method according to the invention, the deprotection reagents are aqueous, allowing for good droplet formation on a wide variety of array substrate surfaces. Moreover, because the selection of features employs aqueous media, small-scale discrete droplet application onto specified array addresses can be carried out by adaptation of techniques for reproducible fine droplet deposition from printing technologies.

NOVEL COMPOSITIONS OF MATTER:

The invention additionally provides protected nucleoside monomers as novel compositions of matter useful, inter alia, in the synthesis of oligonucleotides as described herein. The novel monomers have the structural formulae (II) and (X)

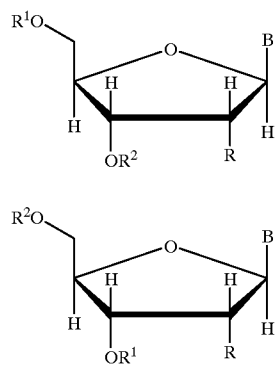

wherein:

B is a purine or pyrimidine base, as described previously herein;

R is hydrido or hydroxyl;

R$^1$ is COOR$^3$ wherein R$^3$ is as described previously herein, such that the moiety OR$^1$ represents a carbonate-protected hydroxyl group; and R$^2$ is a phosphorus derivative phosphorus derivative that enables coupling to a free ydroxyl group, and is preferably a phosphoramidite having the structure (III)

wherein X and Y are as defined earlier herein.

Reagent (II), used for 3'-to-5' synthesis, is readily prepared by reaction of the unprotected nucleoside with the haloformate R$^3$O—(CO)—Hal wherein Hal represents halo, typically chloro, and R$^3$ is as defined previously, in the presence of a base effective to catalyze the nucleophilic reaction, e.g., pyridine. This step results in a 5'-carbonate, as follows:

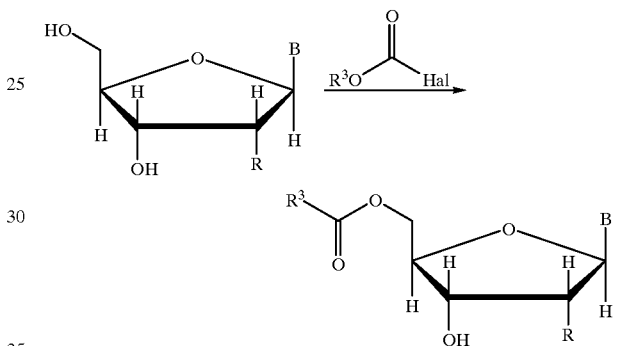

The intermediate so prepared is then phosphitylated with the phosphoramidite PX$_2$(OY) wherein X and Y are as defined earlier, resulting in conversion of the 3'-hydroxyl moiety to the desired substituent —O—PX(PY), i.e., —OR$^2$:

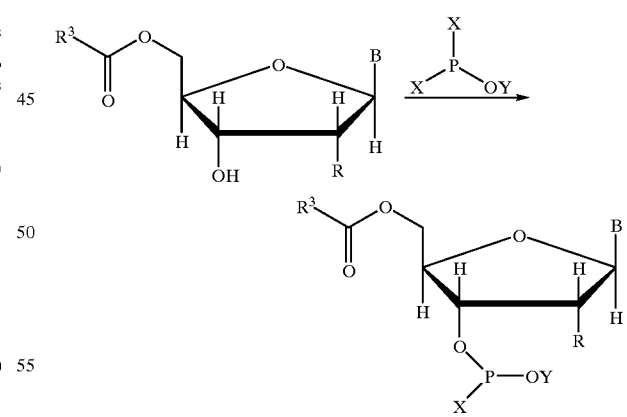

A specific example of this synthesis is illustrated schematically in FIG. 4, wherein "Arco" represents the aryloxycarbonyl group p-chlorophenylcarbonyl, iPr represents isopropyl, and B is either N$^6$-benzoyl-protected deoxyadenine, N$^4$-Fmoc-protected deoxycytidine, N$^2$-isobutyryl-protected deoxyguanine or thymine. In the initial step of the reaction, the unprotected base is reacted with 4-chlorophenyl chloroformate in the presence of pyridine to give the carbonate-protected 5'-OH, followed by phosphitylation using (iPr$_2$N)$_2$PO(CH$_2$)$_2$CN, i.e., β-cyanoethyl-N,N-diisopropylamino phosphoramidite.

Reagent (X), used for 5'-to-3' synthesis, may be prepared by first synthesizing a 5'-protected nucleoside using a conventional 5'-OH protecting group such as DMT. This 5'-protected nucleoside is then reacted with the haloformate R$^3$O—(CO)—Hal, which, as above, is done in the presence of a base effective to catalyze the nucleophilic reaction, e.g., pyridine. The DMT group is then removed with acid, resulting in the 3'-carbonate intermediate

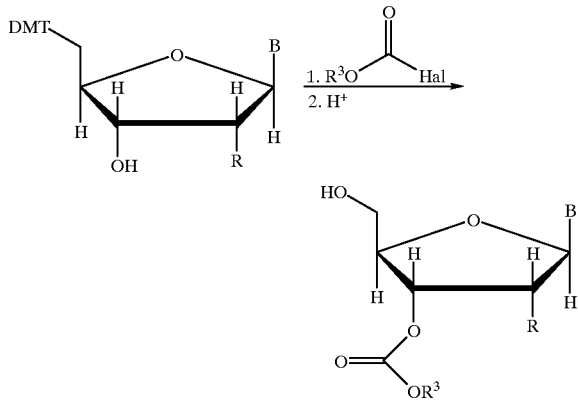

Subsequent reaction with the phosphoramidite results in conversion of the 5'-hydroxyl moiety to the desired substituent —O—PX(PY), i.e., —OR$^2$:

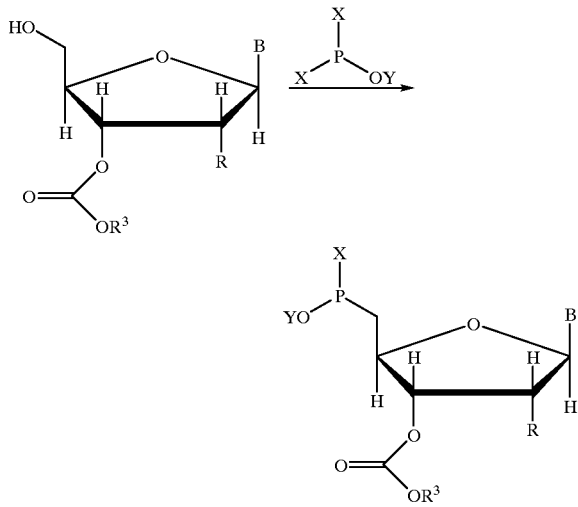

A specific example of this synthesis is illustrated schematically in FIG. 5, wherein, as in FIG. 4, "Arco" again represents the aryloxycarbonyl group p-chlorophenylcarbonyl, iPr represents isopropyl, and B is either N$^6$-benzoyl-protected deoxyadenine, N$^4$-Fmoc-protected deoxycytidine, N$^2$-isobutyryl-protected deoxyguanine or thymine. In the initial step of the reaction shown in FIG. 4, the 5'-O-DMT-protected base is reacted with 4-chlorophenyl chloroformate in the presence of pyridine to give the 3' carbonate, followed by DMT removal using trichloroacetic acid and subsequent phosphitylation using β-cyanoethyl-N,N-diisopropylamino phosphoramidite.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

EXPERIMENTAL:

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

EXAMPLE 1

PROTECTION AND DEPROTECTION OF DEOXYTHYMIDINE (A) GENERAL PROCEDURES:

Nuclear resonance spectra ($^1$H, $^{13}$C and $^{31}$P NMR) were recorded on a Varian VXR-300 spectrometer. Tetramethylsilane was used as an internal reference for $^1$H and $^{13}$C NMR. An external capillary containing 85% H$_3$PO$_4$ was used as a reference for $^{31}$P NMR. Downfield chemical shifts were recorded as positive values for $^{31}$P NMR. Thin layer chromatography was performed on HF254 silica gel plates (Merck) in: CH$_2$Cl$_2$/MeOH, 9:1 (Solvent A), CH$_2$Cl$_2$/MeOH, 8:2 (Solvent B), ethyl acetate/THF/Et$_3$N (45/45/10, v/v/v) (Solvent C). Pyridine, dichloromethane, and benzene were freshly distilled over CaH$_2$. Acetonitrile was distilled over P$_2$O$_5$ (solid), followed by calcium hydride, and stored over molecular sieves. Hexanes and pentanes were distilled. 5'-O-(4,4'- Dimethoxytrityl)-6-N-((di-N-butylanino) methylene)-2'-deoxyadenosine and 2-N-(di-N-butylamino) methylene-2'-deoxyguanosine were prepared according to published procedures. Protected nucleoside-derived CPG was obtained from Applied Biosystems Inc.

(B) SYNTHESIS OF 5'-O-NUCLEOSIDE CARBONATES:

The syntheses were conducted generally as follows. Deoxythymidine (2 mmol) was co-evaporated with anhydrous pyridine (2×20 ml), then redissolved in dry pyridine (40 ml). The corresponding chloroformate (2.2 mmol) was added and the mixture stirred at room temperature (25° C.) for 2 hr. The reaction was quenched with water (1 ml), then concentrated. The residual pyridine was removed by co-evaporation with toluene (40 ml).

The resulting residue was then dissolved in CHCl$_3$ (50 ml) and extracted with brine (40 ml). The aqueous layers were back-extracted with CHCl$_3$ (30 ml). The organic layers were combined, concentrated, and then loaded onto a silica gel column (100 g). The column was eluted with CH$_2$Cl$_2$ using a methanol gradient. The isolated products were evaporated to foams.

This scheme was used to synthesize a series of alkyl and aryl 5'-O-carbonates of deoxythymidine from the corresponding chloroformates. In all cases, the best yields for the 5'-protected nucleoside were obtained when the reactions were performed at room temperature in pyridine using a slight excess of the chloroformate (1.1 eq). Under these conditions, good regioselectivity was observed with most chloroformates. Table 1 sets forth isolated yields of the 5'-protected nucleosides:

TABLE 1

ISOLATED YIELDS OF 5'-PROTECTED DEOXYTHYMIDINE WITH VARIOUS ALKYL AND ARYL CHLOROFORMATES AT ROOM TEMPERATURE IN PYRIDINE

| 5'-Carbonate Protected Thymidine | Isolated Yield |
|---|---|
| $Cl_3C(CH_3)_2COCO_2$-dT (1a) [5'-O-TCBOC-dT] | 87% |
| [5'-O-Fmoc-dT] (1b) | 90% |
| 2-$(NO_2)C_6H_4OCO_2$-dT (1c) [5'-O-oNPh-dT] | 35% |
| $C_6H_5N=NC_6H_4OCO_2$-dT (1d) [5'-O-PAP-dT] | 50% |
| $C_6H_5OCO_2$-dT (1e) [5'-O-Ph-dT] | 60% |
| 4-$(Cl)C_6H_4OCO_2$-dT (1f) [5'-O-pClPh-dT] | 60% |

The results were as follows.

5'-O-(2,2,2-Trichloro-1,1-Dimethylcarbonyl)Deoxythymidine (5'-O-TCBOC-dT, 1a):

Yield 87%. $R_F$(A)=0.40, $R_F$(B)=0.70. $^1$H NMR (CDCl$_3$+DMSO-D$_6$) δ: 7.33 (d, 1, H$_6$), 6.34 (t, J=7 Hz, 1, H$_{1'}$), 4.45–4.08 (m, 4, H$_{3'}$, H$_{4'}$, H$_{5,5'}$) 2.32–2.1 (m, 2, H$_{2,2'}$), 1.94–1.93 (m, 6, C—(CH$_3$)$_2$),1.88 (s, 3, C$^5$5-CH$_3$). $^{13}$C NMR (CDCl$_3$+DMSO-D$_6$) δ: 163.27 (C-4),150.93 (O—(CO)—O), 149.68 (C-2),134.21 (C-6), 109.71 (C-5), 104.37 C—Cl$_3$), 88.64 (C—Me$_2$), 83.39 (C-4'), 82.94 (C-1'), 62.96 (C-3'), 66.4 (C-5'), 20.02, 19.95 (C—(CH$_3$)$_2$), 11.6 (C$^5$—CH$_3$).

5'-O-(9-Fluorenylmethylcarbonyl)Deoxythymidine (5'-O-Fmoc-dT, 1b):

Yield 90%. $R_F$(A)=0.41, $R_F$(B)=0.74. $^1$H NMR (CDCl$_3$+DMSO-D$_6$) δ: 7.72–7.28 (m, 9, Fmoc+H$_6$), 6.36 (t, J=7 Hz, 1, H$_{1'}$), 4.54–4.11 (m, 3, CHCH$_2$ (Fmoc), H$_{3'}$, H$_{4'}$, H$_{5,5'}$) 2.35–2.06 (m, 2, H$_{2,2'}$) 1.79 (s, 3, C$^5$—CH$_3$). $^{13}$C NMR (CDCl$_3$+DMSO-D$_6$) δ: 163.87 (C-4), 154.58 (C-2), 150.28 (O—(CO)—O), 142.76, 142.71, 140.91, 127.04, 126.82, 124.59, 119.75 (Fmoc), 134.89 (C-6), 110.55 (C-5), 84.29 (C- 4'), 83.76 (C-1'), 69.47 (C-3'), 66.92 (C-5'), 46.3 (Fmoc), 39.86 (C-2'), 12.13 (C$^5$—CH$_3$).

5'-O-(o-Nitrophenylcarbonyl)Deoxythymidine (5'-O-oNPh-dT, 1c):

Yield 35%. $R_F$ (A)=0.41, $R_F$ (B)=0.68. $^1$H NMR (CDCl$_3$) δ: 8.21 (d, 1, H$_6$), 7.89–7.53 (m, 4, aryl), 6.37 (t, J=7 Hz, 1, H$_{1'}$), 4.53–4.17 (m, 4, H$_{3'}$, H$_{4'}$, H$_{5,5'}$), 2.33–2.03 (m, 2, H$_{2,2'}$) 1.79 (s, 3, C$^5$5—CH$_3$). $^{13}$C NMR (CDCl$_3$) δ: 164.3 (C-4), 153.04 (O—(CO)—O), 152.21 (C-2), 144.68, 142.1, 136.5, 128.36, 126.65, 125.68 (C$_6$H$_4$), 136.33 (C-6), 111.05 (C-5), 85.44 (C-1'), 84.62 (C-4', 71.54(C-5'), 69.67 (C-3'), 40.15 (C-2'), 12.4 (C$_5$—CH$_3$).

5'-O-(p-Phenylazophenylcarbonyl)Deoxythymidine (5'-O-PAP-dT, 1d):

Yield 50%. $R_F$ (A)=0.41, $R_F$ (B)=0.75. $^1$H NMR (CDCl$_3$) δ: 7.94–7.28 (m, 10, H$_6$6+aryl(PAP)), 6.31 (t, J=7 Hz, 1, H$_{1'}$), 4.5–4.12 (a, 4, H$_{3'}$, H$_{4'}$, H$_{5,5'}$), 2.33–2.19 (m, 2, H$_{2,2'}$), 1.86 (s, 3, C$_5$—CH$_3$). $^{13}$C NMR (CDCl$_3$) δ: 164.44 (C-4), 152.33 (O—(CO)—O), 152.1 (C-2), 152.86, 152.16, 150.55, 150.23, 131.05, 128.84, 123.86, 122.54, 121.21 (PAP), 135.56 (C-6), 110.92 (C-5), 84.65 (C-1'), 83.55 (C-4'), 70.13 (C-5'), 67–53 (C-3'), 39.73 (C-2'), 11.93 (C$^5$—CH$_3$).

5'-O-(Phenylcarbonyl)Deoxythymidine (5'-O-Ph-dT, 1e):

Yield 60%. $R_F$ (A)=0.41, $R_F$ (B)=0.71. $^1$H NMR (CDCl$_3$) δ: 7.54–7.19 (m, 6, H$_6$+aryl), 6.34 (t, J=7 Hz, 1, H$_{1'}$) 4.52–4.12 (m, 4, H$_{3'}$, H$_{4'}$, H$_{5,5'}$), 2.3–2 (a, 2, H$_{2,2'}$), 178 (s, 3, C$^5$—CH$_3$). $^{13}$C NMR (DMSOd-$_6$+(CD$_3$)$_2$CO) δ: 164.36 (C-4), 152.21 (O—(CO)—O), 151.35 (C-2), 154.2, 130.42 126.97, 121.99 (C$_6$H$_4$), 136.61 (C-6), 111.11 (C-5), 85.44 (C-1'), 84.84 (C-4'), 71.73 (C-5'), 68.83 (C-3'), 40.21 (C-2'), 12.5 (C$^5$—CH$_3$).

5'-O-(p-Chlorophenylcarbonyl)Deoxythymidine (5'-O-pClPh-dT, 1f):

Yield 60%. $R_F$ (A)=0.42, $R_F$ (B)=0.73. $^1$H NMR (CDCl$_3$) δ: 7.9 (d, 1, H$_6$), 7.44–7.16 (m, 5, aryl), 6.34 (t, J=7 Hz, 1, H$_{1'}$), 4.6–4.12 (m, 4, H$_{3'}$, H$_{4'}$, H$_{5,5'}$). 2.3–2.05 (m, 2, H$_{2,2'}$), 1.74 (s, 3, C$^5$—CH$_3$). $^{13}$C NMR (CDCl$_3$) δ: 164.4 (C-4), 153.23 (O—(CO)—O), 151.4 (C-2), 149.39, 139.86, 129.73, 122.23 (C$_6$H$_4$), 136.6 (C-6), 111.1 (C-5), 85.41 (C-1'), 84.8 (C-4'), 71.52 (C-5'), 40.25 (C-2'), 12.49 (C$^5$CH$_3$).

(C) SYNTHESIS OF 5'-O-DMT-3'-O-R-DEOXYTHYMIDINES:

The 3'-hydroxyl group of 5'-O-DMT-deoxythymidine was protected with phenyloxycarbonyl (2a), benzoyl (2b), and acetyl (2c), as follows. 5'-O-(4,4'-Dimethoxytrityl)-deoxythymidine (1 mmol) was co-evaporated 3 times with anhydrous pyridine, then redissolved in 20 ml of pyridine. Corresponding chloroformates (1.1 mmol) were added to the nucleoside mixture. After stirring for 6 hr, the reaction was quenched with water (100 ml) and concentrated. Residues of pyridine were removed by co-evaporation with toluene (2×20 ml).

The resulting gum was dissolved in CH$_2$Cl$_2$, extracted with 10% aqueous NaHCO$_3$, and dried over Na$_2$SO$_4$. After concentration, the product was loaded onto a silica gel column (50 g) and eluted with CH$_2$Cl$_2$ using a methanol gradient (0–3%). Product fractions were collected and concentrated to a foam.

The results were as follows.

5'-O-(4,4'-Dimethoxytrityl)-3'-O-Phenylcarbonyl Deoxythymidine (2a):

Yield 80%. $R_F$ (A)=0.74, $R_F$ (B)=0.91. $^1$H NMR (CDCl$_3$) δ: 7.65–6.83 (m, 18, H$_6$+DMTr+aryl), 6.57 (t, J=7 Hz, 1, H$_{1'}$), 5.45 (m, 1, H$_{3'}$) 4.34 (m, 1, H$_{4'}$), 3.79 (s, 6, OCH$_3$), 3.54 (m, 2, H$_{5,5'}$), 2.72–2.52 (m, 2, H$_{2,2'}$), 1.41 (s, 3, C$^5$—CH$_3$).

5'-O-(4,4'-Dimethoxytrityl)-3'-O-Benzoyl Deoxythymidine (2b):

Yield 90%. $R_F$ (A)=0.72, $R_F$ (B)=0.91. $^1$H NMR (CDCl$_3$) δ: 8.07–6.85 (m, 18, H$_6$+DMTr+aryl), 6.58 (t, J=7 Hz, 1, H$_{1'}$), 5.45 (m, 1, H$_{3'}$), 4.14 (m, 1, H$_{4'}$), 3.79 (s, 6, OCH$_3$), 3.57 (m, 2, H$_{5,5'}$) 2.63 (m, 2, H$_{2,2'}$), 1.42 (s, 3, C$^5$—CH$_3$).

5'-O-(4,4'-Dimethoxytrityl)-3'-O-Acetyl Deoxythymidine (2c):

Yield 90%. $R_F$ (A)=0.67, $R_F$ (B)=0.89. 1H NMR (CDCl$_3$) δ: 7.62 (s, 1, H$_6$),7.4–6.82 (m, 13, DMTr), 6.46 (t, J=7 Hz, 1, H$_{1'}$), 5.45 (m, 1, H$_{3'}$), 4.14 (m, 1, H$_{4'}$), 3.78 (s, 6, OCH$_3$), 3.47 (m, 2, H$_{5,5'}$), 2.45 (m, 2, H$_{2,2'}$) 2.08 (s, 3, CO—CH$_3$), 1.39 (s, 3, C$^5$—CH$_3$).

(D) NUCLEOSIDE DEPROTECTION BY PEROXY ANIONS:

Deprotection reactions were carried out using peroxy anions on alkyl and aryl 5'-O-carbonates of deoxythymidine synthesized as described above. The reactions were monitored by TLC for complete conversion of the starting material to deoxythymidine. A wide variety of peroxy anions, known to exhibit strong alpha effects, were screened for their ability to cleave 5'-O-carbonates of deoxythymidine. Peroxy anion solutions active in cleavage of the 5'-O-carbonates were buffered at a variety of pH conditions. The cleavage activity of these peroxy anion solutions was shown to be rapid only at pH conditions above the pKa for the formation of the anion. The ability of peroxy anion solutions A, B, C, D and E to completely deprotect the 5'-O-carbonates of deoxythymidines 1a–1f is summarized in Table 2.

Solution A: 3.1% LiOH•H$_2$O (10 mL), 1.5 M 2-amino-2-methyl-1-propanol ("AMP"), pH 10.3 (15 mL), 1,4-dioxane (50 mL), 30% H$_2$O$_2$ (12 mL), pH 12.0.

Solution B: 3.1% LiOH•H$_2$O (10 mL), 1.5 M 2-amino-2-methyl-1-propanol ("AMP"), pH 10.3 (15 mL), dimethyl sulfoxide ("DMSO") (50 mL), 30% H$_2$O$_2$ (12 mL), pH 12.0.

Solution C: 3.1% LiOH•H$_2$O (10 mL), 1.5 M 2-amino-2-methyl-1-propanol ("AMP"), pH 10.3 (15 mL), 1,4-dioxane (50 mL), 30% H$_2$)$_2$ (12 mL), pH 12.0, m-chloroperbenzoic acid ("mCPBA") (1.78 g), pH 9.6.

Solution D: H$_2$O (10 mL), dioxane (50 mL), 2.5 M Tris (15 mL), H$_2$O$_2$ (12 mL), mCPBA (1.78 g), pH 9.0.

Solution E: H$_2$O (10 mL), dioxane (50 mL), 2.5 M Tris (15 mL), t-butyl-OOH (0.1 M), pH 9.0.

TABLE 2

TIMES REQUIRED FOR COMPLETE CONVERSION OF PROTECTED NUCLEOSIDES 1A THROUGH 1F USING PEROXY ANION SOLUTIONS A, B, C, D AND E

| 5'-Carbonate-dT Compounds | Reaction Completion Times for Deprotection Solutions | | | | |
|---|---|---|---|---|---|
| | A | B | C | D | E |
| 1a | <1 min | <1 min | <12 min | — | — |
| 1b | >1 hr | <1 min | >3 hr | — | — |
| 1c | <1 min | <1 min | <1 min | — | |
| 1d | <1 min | <1 min | <1 min | <1 min | >12 hr |
| 1e | <1 min | <1 min | <1 min | <2 min | <12 hr |
| 1f | <1 min | <1 min | <1 min | <1 min | <12 hr |

(E) SELECTIVITY OF VARIOUS PEROXY ANION SOLUTIONS FOR DEPROTECTION OF CARBONATES:

As described in part (C) of this example, the 3'-hydroxyl group of 5'-O-DMT-deoxythymidine was protected with a phenyloxycarbonyl (2a), a benzoyl (2b), and an acetyl (2c) group. The stability of these 3'-protecting groups was determined by TLC using deprotection conditions C and D (Table 2). Under both these conditions, the phenyl carbonate was completely removed in less than 2 min. The 3'-benzoyl group was completely stable under both conditions for 140 min. The 3'-acetyl group was cleaved to a small extent (less than 3%) over the 140 min exposure to deprotection condition A (pH 10.0). The 3-benzoyl group was completely stable for the 140 min exposure to condition B.

(F) SELECTIVITY OF DEPROTECTION ON SOLID-SUPPORT ATTACHED NUCLEOSIDES:

The demonstration of stability at the 3' position was then extended to the succinate linker commonly used for the attachment of nucleosides to Controlled Pore Glass, as follows. 5'-DMT-deoxythymidine attached to Long Chain Alkyl Amine Controlled Pore Glass (LCAA/CPG) through a 3'-succinate linkage was obtained from a commercial source. This solid-support attached nucleoside was then exposed to deprotection conditions A through D. The stability of the 3'-linkage was determined spectrophotometrically based upon the evolution of the trityl cation during subsequent treatment with toluene sulfonic acid in anhydrous acetonitrile. Deprotection conditions A and B gave complete cleavage of the 3'-succinate in 20 min. Deprotection conditions C and D gave less than 2% cleavage of the 3'-succinate after 20 hrs.

EXAMPLE 2

SIMULTANEOUS OLIGOTHYMIDYLATE DEPROTECTION AND INTERNUCLEOTIDE BOND OXIDATION BY PEROXY ANIONS (A) OLIGONUCLEOTIDE SYNTHESIS ON CONTROLLED PORE GLASS:

Oligonucleotides were synthesized on CPG using an automated DNA synthesizer (ABI model 380A). The synthesis cycle used for 5'-DMT protected nucleoside phosphoramidites (Cycle 1) is shown in Table 4. This cycle was initially modified for the use of 5'-carbonate protected nucleoside phosphoramidites simply by substituting the alternative deprotection mixtures for the 3% TCA solution (Step 8, Table 4) and varying the exposure times. For the synthesis of longer sequences using 5-carbonate protected nucleoside phosphoramidites, it was necessary to separate the deprotection mixture into a two-component system (Table 3). The separation of the deprotection mixture was accomplished using the capping ports on the synthesizer, and thus necessitated elimination of the capping step from the synthesis cycle. Table 4 shows the optimized cycle for synthesis using 5'-carbonate protected nucleoside phosphoramidites (Cycle 2):

TABLE 3

TWO-COMPONENT SYSTEM FOR STORAGE OF DEPROTECTION SOLUTION C

| | |
|---|---|
| C-1 | Solution 30% H$_2$O$_2$ (10 ml), LiOH (280 mg), dioxane (7.5 ml), 2.5 M Tris-Base (15 ml), water (42.5 ml) |
| C-2 | Solution 50–60% mCPBA (1.78 g), dioxane (42.5 ml) |

TABLE 4

OLIGONUCLEOTIDE SYNTHESIS CYCLES

| Step # | Function | Reagent | Cycle 1 Time, sec. | Cycle 2 Time, sec. |
|---|---|---|---|---|
| 1 | Wash | Acetonitrile | 25 | 25 |
| 2 | Coupling | Amidite (0.15 M, 30 eq) Tetrazole (0.5 M, 120 eq) in Anhydrous Acetonitrile | 2 × 30 | 2 × 30 |
| 3 | Wash | Acetonitrile | 5 | 5 |
| 4 | Capping | N-Methylimidazole/2,6-Lutidine/ Acetic Anhydride/THF (1/1/1/2, vol/vol/vol/vol) | 40 | — |
| 5 | Oxidation | 0.1 M I$_2$ in THF/Lutidine/Water (80/40/2, vol/vol/vol) | 30 | — |
| 6 | Wash | Acetonitrile | 25 | — |
| 7 | Wash | Dichloromethane (Cycle 1) 1,4-Dioxane (Cycle 2) | 25 | 25 |
| 8 | Deblock | 3% TCA in CH$_2$C$_2$ (Cycle 1) 1:1 mix of Solution C-1 & Solution C-2 from Table 3 (Cycle 2) | 2 × 30 | 480 |
| 9 | Wash | Dichloromethane (Cycle 1) 1,4-Dioxane (Cycle 2) | 25 | 25 |

(B) ANALYSIS OF OLIGONUCLEOTIDES BY HPLC:

The oligonucleotides synthesized on the solid support were deprotected with concentrated ammonium hydroxide (55° C., 24 hr). The ammonium hydroxide solutions were removed from the support and evaporated to dryness. The crude oligonucleotides were reconstituted in distilled water and stored at −20° C.

HPLC analysis was performed by ion-exchange HPLC (Nucleogen 60-7DEAE, 4 mm ID×125 mm). Oligonucleotides were eluted from the column with a LiCl gradient (0.0–0.7 M) in a water/acetonitrile (60/40, v/v) buffer containing sodium acetate (0.002 M, pH 6.0).

(C) SOLID-SUPPORT DEPROTECTION OF 5'-O-CARBONATES OF THYMIDINE:

The deprotection efficiency of peroxy-anion solutions on oligonucleotides was determined by the synthesis of oligothymidylate tetramers. The 5'-O-arylcarbonates of deoxythymidine (see part (B) of Example 1, compounds 1a through 1f) were converted to the corresponding 3'-O-(2-cyanoethyl)-N,N-diisopropylphosphoramidite by procedures described generally in A. D. Barone et al. (1984) *Nucleic Acids Res.* 12:4051, as follows.

Synthesis of the 2-cyanoethyl-N,N,N',N'-tetraisopropylphosphorodiamidite phosphine was performed according the procedure described in A. Kraszewski et al. (1987) *Nucleic Acids Res.* 18:177. The resulting product was purified by distillation from CsF. The product was obtained in 60% yield. Purity was confirmed by $^{31}$P NMR (CDCl$_3$) δ: 123.8 ppm.

Thymidyl-3'-5'-deoxythymidine was synthesized on solid-support using 5'-O-dimethoxytrityl-3'-O-(2-cyanoethyl)-N,N-diisopropylaminodeoxythymidinephosphoramidite. The dimer was elongated to a trimer using a 5'-O-aryloxycarbonyl-3'-O-(2-cyanoethyl)-N,N-diisopropylaminodeoxythymidinephosphoramidite and synthesis cycle 1 (Table 4). Deprotection of the carbonate was then attempted using deprotection mixture C, at 1 min increments, from 1–15 min. The extent of deprotection was determined by the yield of the subsequent coupling reaction using a standard 5'-DMT-dT phosphoramidite. Deprotection efficiency for the 5'-O-arylcarbonate was determined using ion-exchange HPLC. The percent deprotection was calculated by integration and normalization of peak areas for the corresponding trimers and tetramers, assuming quantitative coupling reactions. The optimum deprotection time and extent of deprotection for each aryloxycarbonyl group is summarized in Table 5.

TABLE 5

OPTIMUM DEPROTECTION TIMES DETERMINED FOR 5'-ARYLCARBONATES OF THYMIDINE ON CONTROLLED PORE GLASS USING DEPROTECTION SOLUTION C

| 5'-Carbonate dT Compounds | Optimum Deprotection Time | Deprotection Efficiency |
| --- | --- | --- |
| 1c | 5 min | 80% |
| 1d | 1 min | 94% |
| 1e | 7 min | 98% |
| 1f | 3 min] | 98% |

(D) SOLID SUPPORT SYNTHESIS AND INTERNUCLEOTIDE BOND OXIDATION:

Several oligothymidylate tetramers were synthesized on Controlled Pore Glass using 5'-O-p-chlorophenyloxycarbonyl-3'-O-(2-cyanoethyl)-N,N-diisopropylaminodeoxythymidinephosphoramidite. These syntheses were performed on a 1 μmol scale using an automated DNA synthesizer. The only modification from the standard 1 μmol synthesis cycle (Cycle 1, Table 4) was the use of deprotection mixture C (7 min) in place of 3% TCA in dichloromethane. The resulting tetramers were compared to oligothymidylate tetramers synthesized using the standard DMT protected phosphoramidites of thymidine. These tetramers were then analyzed using ion-exchange HPLC. There were no detectable differences in the yield or purity of any of the oligomers.

Oligothymidylate tetramers were then synthesized using this same synthesis cycle, which was again modified by the removal of the iodine oxidation step. This concomitant deprotection and oxidation cycle produced tetramers of identical yield and purity to the standard DMT phosphoramidite synthesis. Decomposition of MCPBA in the presence of LiOH results in the deprotection mixture being effective for only a few hours. In order to synthesize longer sequences, it was necessary to separate the deprotection mixture into a two component system (Table 3). This was accomplished using the capping ports on the automated DNA synthesizer. Separating the LiOH from the mCPBA and mixing just prior to deprotection allows the reagents to remain effective for several days. Oligonucleotide synthesis using 5'-O-arylcarbonate nucleoside phosphoramidites was carried out with and without acetic anhydride capping. No adverse effects on the yield of final product or increases in the appearance of n-1 products were observed in absence of capping. This is contrary to what is seen with the use of DMT protected phosphoramidites in the absence of capping. Anion-exchange HPLC profiles of crude synthesis products of oligothymidylate decamers were produced. Product purity and yield of full-length oligonucleotides, using peroxyanion deprotection of 5'-O-carbonates in absence of acetic anhydride capping and iodine oxidation (Cycle 2, Table 4), were comparable to or better than those obtained using DMT phosphoramidites and the standard synthesis cycle.

EXAMPLE 3

PEROXY ANION DEPROTECTION OF 5'-O-DMT-PROTECTED CYTOSINE, ADENINE, URACIL, THYMIDINE AND GUANOSINE NUCLEOSIDES

The unprotected heterocyclic bases cytosine and adenine are susceptible to N-oxidation by peracids and peroxides under stringent conditions, and oxidative reactions that result in ring cleavage of uracil, thymidine and guanosine in the presence of highly concentrated peroxides at elevated temperatures have been described. 5'-O-DMT-protected nucleosides, N-protected with a (di-N-butylamino) methylene group, were dissolved in deprotection mixture C and allowed to react for 24 hrs. The tritylated nucleosides were extracted from the aqueous deprotection mixture with CHCl$_3$ and analyzed by $^{13}$C NMR and TLC. Neither formation of N-oxides nor attack at the 5,6-double bond of thymidine (leading to ring cleavage) was detected.

EXAMPLE 4

SYNTHESIS OF MIXED OLIGONUCLEOTIDES

This example demonstrates extension of the method of the invention to synthesis of mixed oligonucleotide sequences, employing substituted aryl carbonate protected phosphoramidite synthons, and following each coupling reaction by treatment with a mixture of peroxy-anions at mild pH (less than 10) to deprotect and concomitantly oxidize the internucleotide linkage.

The method is high-yielding, and effective for the four main 2'-deoxynucleotides. Synthesis in both the 3'–5' direction and the 5'–3' direction were carried out, with equal effect.

(A) PROTECTED PHOSPHORAMIDITE SYNTHESIS:

Generally, the protected nucleoside phosphoramidites were prepared as follows. The 3'- or 5'-protected nucleoside (5.00 mmol) and tetrazole (175 mg, 2.50 mmol) were dried under vacuum for 24h and then dissolved in trichloromethane (100 mL). 2-cyanoethyl-N,N,N',N'-tetraisopropyl phosphane (2.06 mL, 6.50 mmol) was added in one portion and the mixture stirred over 1 hour. The reaction mixture was washed with sat. NaHCO$_3$ (150 mL) and brine (150 mL), dried over MgSO$_4$ and applied directly to the top of a silica column equilibrated with hexanes. The dichloromethane was flashed off the column with hexanes, and the product eluted as a mixture of diastereoisomers using 1/1 hexanes/ethyl acetate then ethyl acetate. After evaporation of solvents in vacuo and coevaporation with dichloromethane, products were isolated as friable, white, glassy solids in yields varying from 70% to 90%.

The four 5'-aryloxycarbonyl-3'-nucleoside phosphoramidites were prepared by the straightforward two-step procedure shown generally in FIG. 4. In a first step, commercially available base protected 2'-oligodeoxynucleosides were selectively aryl carbonate protected at the 5' position by treatment with 4-chlorophenyl chloroformate in dilute anhydrous pyridine to yield 5'-aryloxycarbonyl protected compounds in moderate to good yield. The use of more concentrated reaction mixtures resulted in an increase in the amounts of isolated 3'- and 3', 5'-bis-aryloxycarbonyl-protected materials. In a second step, the resulting compounds were phosphitylated using the method described in Barone et al., supra, to furnish high yields following column chromatography.

Synthesis of the four 3'-aryloxycarbonyl-5'-nucleoside phosphoramidites were prepared by the three-step procedure shown in FIG. 5.

(C) DEPROTECTION MIXTURE:

The deprotection mixture was formulated in two parts, which were mixed immediately prior to use. Solution F: 3.1% w/v lithium hydroxide monohydrate (10 mL), 1.5 M 2-amino-2-methyl-1-propanol pH 10.3 (15 mL), 1,4 dioxane (17.5 mL). Solution G: 1,4-dioxane (32.5 mL), 50–83% 3-chloroperbenzoic acid (1.78 g), 30% hydrogen peroxide (12 mL). The initial pH of the deprotection mixture was 9.6±0.05. For pH dependence studies, the initial deprotection mixture was altered by varying the strength of the lithium hydroxide solution.

(D) SYNTHESIS OF MIXED-SEQUENCE OLIGONUCLEOTIDES:

A series of model oligodeoxynucleotides was synthesized, having sequences 3'-T$_3$AT$_2$AT$_3$-5', 3'-T$_3$CT$_2$CT$_3$-5', 3'-T$_3$GT$_2$GT$_3$-5', 3'-TACGT-5', 3'TACGTACGT-5', 3'-TA-T-5', 5'-TACGT-3', 5'-TACGTACGT-3', and 5'-CAGTTGTAAACGAGTT-3' (SEQ ID NO:1) HPLC analysis was performed as described in Example 2, part (B); HPLC traces of the all products confirmed the results.

The HPLC obtained for 5'-CAGTTGTAAACGAGTT-3' (SEQ ID NO:1) is shown in FIG. 6. The calculated molecular weight for 5'-CAGTTGTAAACGAGTT-3' (SEQ ID NO:1) is 4921.1; the actual molecular weight determined using MALDI (Matrix Absorption Laser Desorption Ionization) TOF (Time of Flight) analysis was 4921.9. The MALDI TOF spectrum is shown in FIG. 7.

(E) STABILITY OF BASE PROTECTING GROUPS IN THE DEPROTECTION MIXTURE:

The stability of the standard base protecting groups $A^{Bz}$, $C^{Bz}$, and $G^{ibu}$ during exposure to the deprotection mixture was tested by incubating 5'-DMT base-protected deoxynucleosides at room temperature with a large excess of the deprotection mixture. The extent of cleavage of the base protecting groups over time was measured by TLC. The approximate $T_{1/2}$ values for $A^{Bz}$, $C^{Bz}$, and $G^{ibu}$ were approximately ½ hour, 2 hours, and 1 day, respectively, and unlikely to present difficulties for syntheses.

What is claimed is:

1. A method for synthesizing oligonucleotides which comprises (a) condensing the 3'-OH or 5'-OH group of a support-bound nucleoside or oligonucleotide with a monomeric nucleoside phosphoramidite having a carbonate-protected hydroxyl group, to provide an intermediate in which the support-bound nucleoside or oligonucleotide is bound to the monomeric nucleoside through a phosphite triester linkage, and (b) treating the intermediate provided in step (a) with a deprotecting reagent effective to convert the carbonate-protected hydroxyl group to a free hydroxyl moiety and simultaneously oxidize the phosphite triester linkage to give a phosphotriester linkage.

2. The method of claim 1, wherein steps (a) and (b) are carried out in aqueous solution.

3. The method of claim 1, wherein step (b) is conducted at neutral to mildly basic pH.

4. The method of claim 3, wherein the deprotecting reagent used in step (b) comprises a nucleophile having a nucleophilic site and a lone electron pair on an atom adjacent to the nucleophilic site.

5. The method of claim 3, wherein step (b) is conducted at a pH of less than about 10.

6. The method of claim 1, wherein the nucleophile is a peroxide.

7. The method of claim 6, wherein the peroxide is an inorganic peroxide of the formula $M^+OOH^-$, wherein $M^+$ is a counterion.

8. The method of claim 7, wherein the counterion is selected from the group consisting of $H^+$, $Li^+$, $Na^+$, $K^+$, $Rb^+$ and $Cs^+$.

9. The method of claim 6, wherein the peroxide is an organic peroxide of the formula ROOH, wherein R is hydrocarbyl optionally substituted with one or more nonhydrocarbyl substituents and optionally containing one or more nonhydrocarbyl linkages.

10. The method of claim 9, wherein the peroxide has the structure of formula (V), (VI) or (VII)

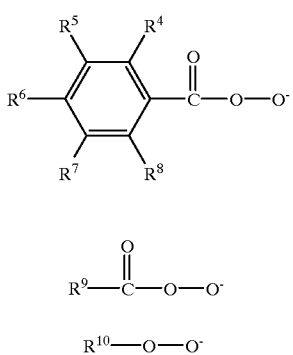

in which $R^4$ through $R^{10}$ are hydrocarbyl optionally substituted with one or more nonhydrocarbyl substituents and optionally containing one or more nonhydrocarbyl linkages.

11. The method of claim 6, wherein the peroxide is one of t-butyl hydroperoxide, m-chloroperoxybenzoic acid, and mixtures thereof.

12. The method of claim 4, wherein step (b) is conducted at a pH that is greater than the pKa of said nucleophile.

13. The method of claim 1, wherein steps (a) and (b) are repeated until an oligonucleotide having a desired sequence and length is provided.

14. The method of claim 1, wherein synthesis is conducted in the 3'-to-5' direction, and step (a) involves condensation at the 5'-OH of the support-bound nucleoside or oligonucleotide.

15. The method of claim 14, wherein the monomeric nucleoside phosphoramidite has the structure of formula (II)

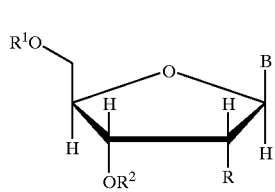

wherein:
B is a purine or pyrimidine base;
R is hydrido or hydroxyl;
$R^1$ is $COOR^3$, wherein $R^3$ is substituted or unsubstituted hydrocarbyl;
$R^2$ has the structure (III)

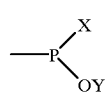

wherein X is $NQ^1Q^2$ in which $Q^1$ and $Q^2$ are independently selected from the group consisting of alkyl, aryl, aralkyl, alkaryl, cycloalkyl, alkenyl, cycloalkenyl, alkynyl or cycloalkynyl, optionally containing one or more nonhydrocarbyl linkages and optionally substituted on one or more available carbon atoms with a nonhydrocarbyl substituent, or wherein $Q^1$ and $Q^2$ are linked to form a mono- or polyheterocyclic ring, and Y is hydrido or hydrocarbyl.

16. The method of claim 15, wherein X is di(lower alkyl)amino or morpholino and Y is selected from the group consisting of lower alkyl, electron-withdrawing β-substituted aliphatic, electron-withdrawing substituted phenyl, and electron-withdrawing substituted phenylethyl.

17. The method of claim 16, wherein Y is selected from the group consisting of methyl, β-cyanoethyl and 4-nitrophenylethyl.

18. The method of claim 15, wherein $R^1$ is selected from the group consisting of o-nitrophenylcarbonyl, p-phenylazophenylcarbonyl, phenylcarbonyl, p-chlorophenylcarbonyl, 5'-(α-methyl-2-nitropiperonyl) oxycarbonyl ("MeNPOC"), 9-fluorenylmethylcarbonyl ("Fmoc"), 2,2,2-trichloro-1,1-dimethylcarbonyl ("TCBOC") and cyano-substituted lower alkyl carbonates.

19. The method of claim 16, wherein $R^1$ is selected from the group consisting of o-nitrophenylcarbonyl, p-phenylazophenylcarbonyl, phenylcarbonyl, p-chlorophenylcarbonyl, 5'-(α-methyl-2-nitropiperonyl) oxycarbonyl ("MeNPOC"), 9-fluorenylmethylcarbonyl ("Fmoc"), 2,2,2-trichloro-1,1-dimethylcarbonyl ("TCBOC") and cyano-substituted lower alkyl carbonates.

20. The method of claim 17, wherein $R^1$ is selected from the group consisting of o-nitrophenylcarbonyl, p-phenylazophenylcarbonyl, phenylcarbonyl, p-chlorophenylcarbonyl, 5'-(α-methyl-2-nitropiperonyl) oxycarbonyl ("MeNPOC"), 9-fluorenylmethylcarbonyl ("Fmoc"), 2,2,2-trichloro-1,1-dimethylcarbonyl ("TCBOC") and cyano-substituted lower alkyl carbonates.

21. The method of claim 15, wherein $R^3$ comprises a moiety that becomes fluorescent or colored upon cleavage of the carbonate $—OCOOR^3$.

22. The method of claim 1, wherein synthesis is conducted in the 5'-to-3' direction, and step (a) involves condensation at the 3'-OH of the support-bound nucleoside or oligonucleotide.

23. The method of claim 22, wherein the monomeric nucleoside phosphoramidite has the structure of formula (X)

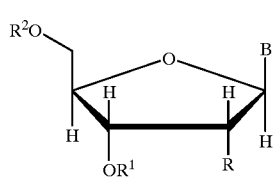

wherein:

B is a purine or pyrimidine base;

R is hydrido or hydroxyl;

$R^1$ is $COOR^3$, wherein $R^3$ is substituted or unsubstituted hydrocarbyl;

$R^2$ has the structure (III)

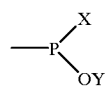
(III)

wherein X is $NQ^1Q^2$ in which $Q^1$ and $Q^2$ are independently selected from the group consisting of alkyl, aryl, aralkyl, alkaryl, cycloalkyl, alkenyl, cycloalkenyl, alkynyl or cycloalkynyl, optionally containing one or more nonhydrocarbyl linkages and optionally substituted on one or more available carbon atoms with a nonhydrocarbyl substituent, or wherein $Q^1$ and $Q^2$ are linked to form a mono- or polyheterocyclic ring, and Y is hydrido or hydrocarbyl.

24. The method of claim 23, wherein X is di(lower alkyl)amino or morpholino and Y is selected from the group consisting of lower alkyl, electron-withdrawing β-substituted aliphatic, electron-withdrawing substituted phenyl, and electron-withdrawing substituted phenylethyl.

25. The method of claim 24, wherein Y is selected from the group consisting of methyl, β-cyanoethyl and 4-nitrophenylethyl.

26. The method of claim 23, wherein $R^1$ is selected from the group consisting of o-nitrophenylcarbonyl, p-phenylazophenylcarbonyl, phenylcarbonyl, p-chlorophenylcarbonyl, 5'-(α-methyl-2-nitropiperonyl)oxycarbonyl ("MeNPOC"), 9-fluorenylmethylcarbonyl ("Fmoc"), 2,2,2-trichloro- 1,1-dimethylcarbonyl ("TCBOC") and cyano-substituted lower alkyl carbonates.

27. The method of claim 24, wherein $R^1$ is selected from the group consisting of o-nitrophenylcarbonyl, p-phenylazophenylcarbonyl, phenylcarbonyl, p-chlorophenylcarbonyl, 5'-(α-methyl-2-nitropiperonyl)oxycarbonyl ("MeNPOC"), 9-fluorenylmethylcarbonyl ("Fmoc"), 2,2,2-trichloro-1,1-dimethylcarbonyl ("TCBOC") and cyano-substituted lower alkyl carbonates.

28. The method of claim 25, wherein $R^1$ is selected from the group consisting of o-nitrophenylcarbonyl, p-phenylazophenylcarbonyl, phenylcarbonyl, p-chlorophenylcarbonyl, 5'-(α-methyl-2-nitropiperonyl)oxycarbonyl ("MeNPOC"), 9-fluorenylmethylcarbonyl ("Fmoc"), 2,2,2-trichloro- 1,1-dimethylcarbonyl ("TCBOC") and cyano-substituted lower alkyl carbonates.

29. The method of claim 23, wherein $R^3$ comprises a moiety that becomes fluorescent or colored upon cleavage of the carbonate —$OCOOR^3$.

30. A method for making an oligonucleotide array made up of array features each presenting a specified oligonucleotide sequence at an address on an array substrate, the method comprising steps of:
providing a hydroxyl-derivatized array substrate and treating the array substrate to protect hydroxyl moieties on the derivatized surface from reaction with phosphoramidites,
then iteratively carrying out the steps of (i) applying droplets of a nucleophile having a nucleophilic site and a lone electron pair on an atom adjacent to the nucleophilic site to effect deprotection of hydroxyl moieties at selected addresses and simultaneous oxidation of newly formed internucleotide phosphite triester linkage, and (ii) flooding the array substrate with a medium containing a selected monomeric nucleoside phosphoramidite having a carbonate-protected hydroxyl group, to permit covalent attachment of the selected nucleoside to the deprotected hydroxyl moieties at the selected addresses.

31. The method of claim 30, wherein steps (i) and (ii) are carried out in aqueous solution.

32. The method of claim 29, wherein step (i) is conducted at neutral to mildly basic pH.

33. The method of claim 32, wherein step (b) is conducted at a pH of less than about 10.

34. The method of claim 30, wherein the nucleophile is a peroxide.

35. The method of claim 34, wherein the peroxide is an inorganic peroxide of the formula $M^+OOH^-$, wherein $M^+$ is a counterion.

36. The method of claim 35, wherein the counterion is selected from the group consisting of $H^+$, $Li^+$, $Na^+$, $K^+$, $Rb^+$ and $Cs^+$.

37. The method of claim 34, wherein the peroxide is an organic peroxide of the formula ROOH, wherein R is hydrocarbyl optionally substituted with one or more nonhydrocarbyl substituents and optionally containing one or more nonhydrocarbyl linkages.

38. The method of claim 37, wherein the peroxide has the structure of formula (V), (VI) or (VII)

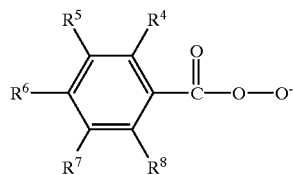
(V)

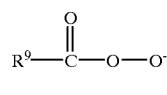
(VI)

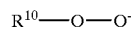
(VII)

in which $R^4$ through $R^{10}$ are hydrocarbyl optionally substituted with one or more nonhydrocarbyl substituents and optionally containing one or more nonhydrocarbyl linkages.

39. The method of claim 34, wherein the peroxide is one of t-butyl hydroperoxide, m-chloroperoxybenzoic acid, and mixtures thereof.

* * * * *

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Test Sequence

<400> SEQUENCE: 1
cagttgtaaa cgagtt                                                   16